US010350289B2

(12) United States Patent
Meyer et al.

(10) Patent No.: US 10,350,289 B2
(45) Date of Patent: Jul. 16, 2019

(54) METHODS OF IMMUNIZATION WITH VARICELLA ZOSTER VIRUS ANTIGEN

(71) Applicant: Merck Sharp & Dohme Corp., Rahway, NJ (US)

(72) Inventors: Brian K. Meyer, New Britain, PA (US); Robert K. Evans, Bangor, ME (US); Channing R. Beals, Solana Beach, CA (US); David C. Kaslow, Seattle, WA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 61 days.

(21) Appl. No.: 14/916,458

(22) PCT Filed: Sep. 2, 2014

(86) PCT No.: PCT/US2014/053657

§ 371 (c)(1),
(2) Date: Mar. 3, 2016

(87) PCT Pub. No.: WO2015/034807

PCT Pub. Date: Mar. 12, 2015

(65) Prior Publication Data

US 2016/0193324 A1 Jul. 7, 2016

Related U.S. Application Data

(60) Provisional application No. 61/873,858, filed on Sep. 5, 2013.

(51) Int. Cl.

| | |
|---|---|
| ***A61K 39/165*** | (2006.01) |
| ***C12N 7/00*** | (2006.01) |
| ***A61K 39/25*** | (2006.01) |
| ***A61K 39/12*** | (2006.01) |
| ***A61K 39/05*** | (2006.01) |
| ***A61K 39/08*** | (2006.01) |
| ***A61K 39/02*** | (2006.01) |
| ***A61K 39/102*** | (2006.01) |
| ***A61K 39/13*** | (2006.01) |
| ***A61K 39/145*** | (2006.01) |
| ***A61K 39/20*** | (2006.01) |
| *A61K 39/00* | (2006.01) |

(52) U.S. Cl.

CPC .............. *A61K 39/25* (2013.01); *A61K 39/05* (2013.01); *A61K 39/08* (2013.01); *A61K 39/099* (2013.01); *A61K 39/102* (2013.01); *A61K 39/12* (2013.01); *A61K 39/13* (2013.01); *A61K 39/145* (2013.01); *A61K 39/165* (2013.01); *A61K 39/20* (2013.01); *C12N 7/00* (2013.01); *A61K 2039/5252* (2013.01); *A61K 2039/5254* (2013.01); *A61K 2039/54* (2013.01); *A61K 2039/55* (2013.01); *C12N 2710/16734* (2013.01); *C12N 2760/16034* (2013.01); *C12N 2760/18434* (2013.01); *C12N 2770/32634* (2013.01); *C12N 2770/36234* (2013.01)

(58) Field of Classification Search

None

See application file for complete search history.

(56) References Cited

U.S. PATENT DOCUMENTS

| | | | | |
|---|---|---|---|---|
| 4,008,317 | A | 2/1977 | Gits | |
| 5,607,852 | A | 3/1997 | Provost et al. | |
| 5,997,880 | A | 12/1999 | Calandra et al. | |
| 6,214,354 | B1 | 4/2001 | Calandra et al. | |
| 2002/0038111 | A1 | 3/2002 | Alchas et al. | |
| 2006/0002949 | A1 | 1/2006 | Glenn et al. | |
| 2008/0091226 | A1 | 4/2008 | Yeshurun et al. | |
| 2009/0043280 | A1 | 2/2009 | Dalton | |
| 2011/0152748 | A1 | 6/2011 | Della Rocca et al. | |
| 2011/0274649 | A1 * | 11/2011 | Kupper | A61K 39/12 424/85.2 |
| 2013/0110043 | A1 | 5/2013 | Levin | |

FOREIGN PATENT DOCUMENTS

| | | |
|---|---|---|
| WO | WO9518852 | 7/1995 |
| WO | WO02083216 | 10/2002 |

(Continued)

OTHER PUBLICATIONS

Trannoy et al. (Vaccine, 2000, vol. 18, p. 1700-1706 in IDS on Oct. 9, 2017).*

Zussman et al, (Clinical Interventions in Aging, 2008, p. 241-250).*

Kim et al. (Current Topics in Microbiology and Microbiology, 2011).*

(Continued)

*Primary Examiner* — Agnieszka Boesen

(74) *Attorney, Agent, or Firm* — Alysia A. Finnegan; Laura M. Ginkel

(57) ABSTRACT

The present invention relates to a method of vaccinating a patient against varicella zoster virus (VZV) by delivery of an effective amount of a live attenuated VZV vaccine to the epidermis or the dermis of a patient's skin at a depth of between about 100 and about 700 microns from the surface of the skin, which is useful for preventing herpes zoster or reducing the severity or duration thereof. In embodiments of the invention, the patient is 50 years of age or older and has been previously exposed to VZV. The invention also relates to a method of preventing VZV infection in an individual who was not previously infected with VZV comprising administering an effective amount of a live attenuated VZV vaccine to the epidermis or the dermis of the individual's skin at a depth of between about 100 and about 700 microns from the surface of the skin.

23 Claims, 13 Drawing Sheets

(56) References Cited

FOREIGN PATENT DOCUMENTS

| | | |
|---|---|---|
| WO | WO02085446 | 10/2002 |
| WO | WO2004026265 | 4/2004 |
| WO | 2008047359 | 4/2008 |
| WO | WO2009048607 | 4/2009 |
| WO | 2010059605 | 5/2010 |
| WO | WO2010067319 | 6/2010 |
| WO | WO2012018973 | 2/2012 |

OTHER PUBLICATIONS

Anonymous: "ZOSTAVAX (Zoster Vaccine Live) Suspension for subcutaneous injection initial US approval 2006", Mar. 25, 2011, pp. 1-12, Retrieved from the internet: URL:https://www.fda.gov/downloads/BiologicsBloodVaccine/Vaccines/ApprovedProducts/UCM285015.pdf.

Berger et al., Decrease of the Lymphoproliferative Response to Varicella-Zoster Virus Antigen in the Aged, Infection and Immunity, 1981, pp. 24-27, vol. 32(1).

Burke et al., Immune Responses to Varicella-Zoster in the Aged, Arch. Inter. Med., 1982, pp. 291-293, vol. 142(2).

Burland et al., Measles vaccination by the intradermal route, Postgrad. Med. Journal, 1969, pp. 323-326, vol. 45 (523).

Centers for Disease Control and Prevention, Use of Combination Measles, Mumps, Rubella, and Varicella Vaccine. Recommendations of the Advisory Committee on Immunization Practices. Morbidity and Mortality Weekly Report, 2010, No. RR-3 (1-16), vol. 59.

Chaussalbel et al., A Modular Analysis Framework for Blood Genomics Studies: Application to Systemic Lupus Erythematosus, Immunity, 2008, pp. 150-164, vol. 29(1).

Etchart et al., Safety and efficacy of transcutaneous vaccination using a patch with the live-attenuated measles vaccine in humans, Vaccine, 2007, pp. 6891-6899, vol. 25.

Fernando et al., Potent Immunity to Low Doses of Influenza Vaccine by Probabilistic Guided Micro-Targeted Skin Delivery in a Mouse Model, PLoS ONE, 2010, pp. e10266 (1-10), vol. 5, No. 4.

Hayward et al., Lymphocyte Responses to Varicella Zoster Virus in the Elderly, Journal of Clincial Immunology, 1987, pp. 174-178, vol. 7(2).

Hickling et al., Intradermal delivery of vaccines: potential benefits and current challenges, Bull. World Health Organ., 2011, pp. 221-226, vol. 89.

Huch et al., Impact of Varicella-Zoster Virus on Dendritic Cell Subsets in Human Skin during Natural Infection, Journal of Virology, 2010, pp. 4060-4072, vol. 84.

Kaplan et al., In vivo function of Langerhans cells and dermal dendritic cells, Trends in Immunology, 2010, pp. 446-451, vol. 31(12).

Keller et al., Purification of individual varicella-zoster virus (VZV) glycoproteins gpl, gpIl, and gpIl1 and their use in ELISA for detection of VZV glycoprotein-specific antibodies, Journal of Virological Methods, 1986, pp. 177-188, vol. 14(2).

Kerzner et al., Safety and Immunogenicity Profile of the Concomitant Administration of Zostavax, Journal of the American Geriatrics Society, 2007, No. 10, pp. 1499-1507, 55.

Kim et al., Delivery Systems for Intradermal Vaccination, Current Topics in Microbiology and Immunology, 2011, pp. 77-112, 351.

Kittan et al., Impaired Plasmacytoid Dendritic Cell Innate Immune Responses in Patients with Herpes Virus-Associated Acute Retinal Necrosis, The Journal of Immunology, 2007, pp. 4219-4230, vol. 179(6).

Klechevsky et al., Functional Specializations of Human Epidermal Langerhans Cells and CD14+ Dermal Dendritic Cells, Immunity, 2008, pp. 497-510, vol. 29(3).

Kok et al., Measles immunization with further attenuated heat-stable measles vaccine using five different methods of administration, Transactions of the Royal Society of Tropical Medicine and Hygiene, 1983, pp. 171-176, vol. 77 (2).

Krah et al., Comparison of gpELISA and neutralizing antibody responses to Oka/Merck live varicella vaccine (Varivax®) in children and adults, Vaccine, 1997, pp. 61-64, vol. 15(1).

Lambert et al., Intradermal vaccine delivery: Will new delivery systems transform vaccine administration?, Vaccine, 2008, pp. 197-208, vol. 26(26).

Lambrecht et al., Mechanism of action of clinically approved adjuvants, Current Opinion Immunology, 2009, pp. 23-29, vol. 21(1).

Levin et al., Immune Response of Elderly Individuals to a Live Attenuated Varicella Vaccine, The Journal of Infectious Diseases, 1992, pp. 253-259, vol. 166.

Liang et al., Longitudinal Data Analysis of Continuous and Discrete Responses for Pre-Post Designs, Sankhyā: The Indian Journal of Statistics, 2000, pp. 134-148, vol. 62, Series B, Part 1.

Miller et al., Intradermal Hepatitis B Virus Vaccine: Immunogenicity and Side-Effects in Adults, The Lancet, 1983, pp. 1454-1456, vol. 24.

Palucka et al., Designing Vaccines Based on Biology of Human Dendritic Cell Subsets, Immunity, 2010, pp. 464-478, vol. 33(4).

Prausnitz et al., Microneedle Based Vaccines, Vaccines for Pandemic Influenza, 2009, pp. 369-393, 333.

Provost et al., Antibody assays suitable for assessing immune responses to live varicella vaccine, Vaccine, 1991, pp. 111-116, vol. 9(2).

Pulendran et al., Systems Vaccinology, Immunity, 2010, pp. 516-529, vol. 33(4).

Querec et al., Systems biology approach predicts immunogenicity of the yellow fever vaccine in humans, Nature Immunology, 2009, pp. 116-125, vol. 10(1).

Reif et al., Genetic Basis for Adverse Events after Smallpox Vaccination, J. Infect. Dis., 2008, pp. 16-22, vol. 198(1).

Roukens et al., Intradermally Administered Yellow Fever Vaccine at Reduced Dose Induces a Protective Immune Response: A Randomized Controlled Non-Inferiority Trial, PLoS ONE, 2008, pp. e1993 (1-8), vol. 3, No. 4.

Takahashi et al, Immunization of the Elderly and Patients with Collagen Vascular Diseases with Live Varicella Vaccine and Use of Varicella Skin Antigen, The Journal of Infectious Diseases, 1992, pp. S58-62, vol. 166 (suppl.).

Trannoy et al., Vaccination of immunocompetent elderly subjects with a live attenuated Oka strain of varicella zoster virus: a randomized, controlled, dose-response trial, Vaccine, 2000, pp. 1700-1706, vol. 18(16).

Wasmuth et al., Sensitive Enzyme-Linked Immunosorbent Assay for Antibody to Varicella-Zoster Virus Using Purified VZV Glycoprotein Antigen, Journal of Medical Virology, 1990, pp. 189-193, vol. 32(3).

Whittle et al., Immunisation of 4-6 Month Old Gambian Infants with Edmonston-Zagreb Measles Vaccine, Lancet, 1984, pp. 834-837, vol. 2 (8407).

A Study of Intradermal Administration of ZOSTAVAX (V211-051 AM2), Clinical Trials Identifier NCT01385566, accessed on Feb. 25, 2016 at https://www.clinicaltrials.gov/ct2/show/results/NCT01385566?term=v211-051&rank=1§=X6015#outcome1.

Arnou et al., Intradermal influenza vaccine for older adults: a randomized controlled multicenter phase III study, Vaccine, 2009, 7304-7312, 27.

Belshe et al., Comparative immunogenicity of trivalent influenza vaccine administered by intradermal or intramuscular route in healthy adults, Vaccine, 2007, 6755-6763, 25(37-38).

Boda et al., Active Immunization of Children Exposed to Varicella Infection in a Hospital Ward Using Live Attenuated Varicella Vaccine Given Subcutaneously or Intracutaneously, Acta Paediatrica Hungarica, 1986, 247-252, 27(3).

Boda, Active Immunisation Against Varicella, The Lancet, 1975, 570, 1.

Gomi et al., Comparison of the complete DNA sequences of the Oka varicella vaccine and its parental virus, Journal of Virology, 2002, 11447-11459, 76(22).

(56) References Cited

OTHER PUBLICATIONS

Gutzeit et al., Identification of an important immunological difference between virulent varicella-zoster virus and its avirulent vaccine: viral disruption of dendritic cell instruction, Journal of Immunology, 2010, 488-497, 185(1).
Holland et al., Intradermal influenza vaccine administered using a new microinjection system produces superior immunogenicity in elderly adults: a randomized controlled trial, Journal of Infectious Diseases, 2008, 650-658, 198(5).
Hung et al., Dose sparing intradermal trivalent influenza (2010/2011) vaccination overcomes reduced immunogenicity of the 2009 H1N1 strain, Vaccine, 2012, 6427-6435, 30.
Kanda et al., Population diversity in batches of the varicella Oka vaccine, Vaccine, 2011, 3293-3298, 29.
Keating, Shingles (herpes zoster) vaccine (zostavax): a review of its use in the prevention of herpes zoster and postherpetic neuralgia in adults aged ≥50 years, Drugs, 2013, 1227-1244, 73.
Krah et al., Enhancement of varicella-zoster virus plaquing efficiency with an agarose overlay medium, Journal of Virological Methods, 1990, 319-326, 27.
Laurent et al., Evaluation of the clinical performance of a new intradermal vaccine administration technique and associated delivery system, Vaccine, 2007, 8833-8842, 25.
Levin, Immune senescence and vaccines to prevent herpes zoster in older persons, Current Opinion in Immunology, 2012, 494-500, 24.
Oxman et al., A Vaccine to Prevent Herpes Zoster and Postherpetic Neuralgia in Older Adults, The New England Journal of Medicine, 2005, 2271-2284, 352(22).
Oxman et al., Zoster Vaccine: Current Status and Future Prospects, Clinical Infectious Diseases, 2010, 197-213, 51(2).
Prieto-Lara et al., New Vaccines and Delivery Strategies for Adult Immunization, Curent Immunology Reviews, 2011, 44-49, 7.
Sanford et al., Zoster Vaccine (Zostavax) A Review of its Use in Preventing Herpes Zoster and Postherpetic Neuralgia in Older Adults, Drugs Aging, 2010, 159-176, 27(2).
Tillieux et al., Complete DNA sequences of two aka strain varicella-zoster virus genomes, Journal of Virology, 2008, 11023-11044, 82(22).
Van Damme et al., Safety and efficacy of a novel microneedle device for dose sparing intradermal influenza vaccination in healthy adults, Vaccine, 2009, 454-459, 27(3).
Weinberg et al., Varicella-Zoster Virus-Specific Immune Responses to Herpes Zoster in Elderly Participants in a Trial of a Clinically Effective Zoster Vaccine, The Journal of Infectious Diseases, 2009, 1068-1077, 200.
Weniger et al., Alternative Vaccine Delivery Methods, Vaccines 5th Edition, 2008, pp. 1357-1392, Chapter 61.
Path (2009) Intradermal delivery of vaccines: a review of the literature and potential for development for use in low-and middle-income countries. PATH/WHO, Ferney Voltaire, France. http://www.path.org/publications/detail.php?=1746.

* cited by examiner

Preliminary Disposition of Subjects

| | Full SC n (%) | 1/3 SC n (%) | Full ID n (%) | 1/3 ID n (%) | 1/10 ID n (%) | 1/27 ID n (%) | Total n (%) |
|---|---|---|---|---|---|---|---|
| Subjects in the Population | 52 | 34 | 34 | 35 | 34 | 34 | 223 |
| **Study Disposition** | | | | | | | |
| COMPLETED | 51 (98.1) | 34 (100) | 34 (100) | 34 (97.1) | 34 (100) | 34 (100) | 221 (99.1) |
| DISCONTINUED | 1 (1.9) | 0 (0) | 0 (0) | 1 (2.9) | 0 (0) | 0 (0) | 2 (0.9) |
| Lost to Follow-Up | 1 (1.9) | 0 (0) | 0 (0) | 0 (0) | 0 (0) | 0 (0) | 1 (0.4) |
| Withdrawal By Subject | 0 (0) | 0 (0) | 0 (0) | 1 (2.9) | 0 (0) | 0 (0) | 1 (0.4) |
| Each Subject was counted once for Study Disposition based on the latest corresponding disposition record. | | | | | | | |

FIG.2

Preliminary Subject Characteristics

| | Full SC n (%) | 1/3 SC n (%) | Full ID n (%) | 1/3 ID n (%) | 1/10 ID n (%) | 1/27 ID n (%) | Total n (%) |
|---|---|---|---|---|---|---|---|
| Subjects in the Population | 52 | 34 | 34 | 35 | 34 | 34 | 223 |
| **Gender** | | | | | | | |
| Female | 31 (59.6) | 20 (58.8) | 17 (50) | 17 (48.6) | 16 (47.1) | 24 (70.6) | 125 (56.1) |
| Male | 21 (40.4) | 14 (41.2) | 17 (50) | 18 (51.4) | 18 (52.9) | 10 (29.4) | 98 (43.9) |
| **Age (Years)** | | | | | | | |
| 50 to 59 | 26 (50) | 16 (47.1) | 17 (50) | 16 (45.7) | 16 (47.1) | 16 (47.1) | 107 (48) |
| 60 and Over | 26 (50) | 18 (52.9) | 17 (50) | 19 (54.3) | 18 (52.9) | 18 (52.9) | 116 (52) |
| Mean | 59.9 | 60.5 | 62.1 | 61.2 | 61.6 | 60.1 | 60.8 |
| SD | 7.7 | 7.5 | 8.5 | 8.7 | 8.1 | 7.1 | 7.9 |
| Median | 59.5 | 60.0 | 59.5 | 60.0 | 60.0 | 60.0 | 60.0 |
| Range | 50 to 83 | 50 to 83 | 51 to 86 | 50 to 81 | 50 to 76 | 50 to 74 | 50 to 86 |
| **Race** | | | | | | | |
| Asian | 1 (1.9) | 0 (0) | 0 (0) | 1 (2.9) | 0 (0) | 0 (0) | 2 (0.9) |
| Black or African American | 2 (3.8) | 0 (0) | 2 (5.9) | 2 (5.7) | 3 (8.8) | 2 (5.9) | 11 (4.9) |
| White | 49 (94.2) | 34 (100) | 32 (94.1) | 32 (91.4) | 31 (91.2) | 32 (94.1) | 210 (94.2) |
| **Ethnicity** | | | | | | | |
| Hispanic or Latino | 39 (75) | 25 (73.5) | 27 (79.4) | 24 (68.6) | 21 (61.8) | 25 (73.5) | 161 (72.2) |
| Not Hispanic or Latino | 13 (25) | 9 (26.5) | 7 (20.6) | 11 (31.4) | 13 (38.2) | 9 (26.5) | 62 (27.8) |

FIG.3

Preliminary Summary of Fold-Rise From Baseline in VZV Antibody Responses Measured by gpELISA at Week 6 Post-Vaccination

| Treatment Group | n | Point Estimate | 90% CI |
|---|---|---|---|
| Full Dose SC | 52 | 1.74 | (1.48, 2.05) |
| 1/3 Dose SC | 34 | 1.64 | (1.35, 2.00) |
| Full Dose ID | 34 | 3.24 | (2.66, 3.94) |
| 1/3 Dose ID | 35 | 2.45 | (2.02, 2.97) |
| 1/10 Dose ID | 34 | 2.21 | (1.82, 2.69) |
| 1/27 Dose ID | 34 | 1.64 | (1.35, 2.00) |

FIG.6

Preliminary Summary of Baseline Titer and VZV Antibody Responses at Week 6 Post-Vaccination Measured by gpELISA

| Timepoint | Treatment Group | N | Point Estimate | 90% CI |
|---|---|---|---|---|
| Baseline | Full Dose SC | 51* | 180.7 | (146.1, 223.5) |
| | 1/3 Dose SC | 34 | 183.3 | (136.8, 245.6) |
| | Full Dose ID | 34 | 260.1 | (183.3, 369.3) |
| | 1/3 Dose ID | 35 | 143.1 | (99.5, 205.8) |
| | 1/10 Dose ID | 34 | 241.4 | (189.0, 308.4) |
| | 1/27 Dose ID | 33* | 193.7 | (151.9, 247.0) |
| Week 6 | Full Dose SC | 51* | 327.3 | (275.1, 389.4) |
| | 1/3 Dose SC | 34 | 310.4 | (246.2, 391.3) |
| | Full Dose ID | 34 | 736.5 | (574.2, 944.6) |
| | 1/3 Dose ID | 35 | 405.6 | (287.2, 572.9) |
| | 1/10 Dose ID | 34 | 483.0 | (388.5, 600.5) |
| | 1/27 Dose ID | 33* | 319.2 | (257.1, 396.3) |
| *Missing value for (1) subject – subjects included in primary cLDA analysis model | | | | |

FIG.7

Preliminary Summary of Fold-Rise From Baseline in VZV Antibody Responses Measured by gpELISA at Week 6 Post-Vaccination By Age Stratum

| Age Stratum | Treatment Group | n | Point Estimate | 90% CI |
|---|---|---|---|---|
| 50 to 59 Years | Full Dose SC | 26 | 1.36 | (1.10, 1.68) |
| | 1/3 Dose SC | 16 | 1.70 | (1.32, 2.20) |
| | Full Dose ID | 17 | 3.45 | (2.68, 4.43) |
| | 1/3 Dose ID | 16 | 2.88 | (2.23, 3.73) |
| | 1/10 Dose ID | 16 | 2.50 | (1.93, 3.24) |
| | 1/27 Dose ID | 16 | 1.72 | (1.33, 2.24) |
| ≥60 Years | Full Dose SC | 26 | 2.16 | (1.70, 2.75) |
| | 1/3 Dose SC | 18 | 1.65 | (1.25, 2.19) |
| | Full Dose ID | 17 | 3.05 | (2.29, 4.08) |
| | 1/3 Dose ID | 19 | 2.12 | (1.61, 2.79) |
| | 1/10 Dose ID | 18 | 1.92 | (1.45, 2.55) |
| | 1/27 Dose ID | 18 | 1.59 | (1.19, 2.12) |

FIG.8

Preliminary Summary of Fold-Rise From Baseline in VZV Antibody Responses Measured by gpELISA at Week 6 Post-Vaccination By Baseline gpELISA Titer

| Baseline gpELISA | Treatment Group | N | Point Estimate | 90% CI |
|---|---|---|---|---|
| ≤205.86 Ab/mL† | Full Dose SC | 29 | 2.54 | (2.00, 3.24) |
| | 1/3 Dose SC | 20 | 2.14 | (1.61, 2.84) |
| | Full Dose ID | 15 | 6.12 | (4.42, 8.47) |
| | 1/3 Dose ID | 16 | 2.91 | (2.12, 3.99) |
| | 1/10 Dose ID | 13 | 3.24 | (2.29, 4.59) |
| | 1/27 Dose ID | 18 | 2.30 | (1.70, 3.09) |
| >205.86 Ab/mL† | Full Dose SC | 22 | 1.19 | (0.98, 1.46) |
| | 1/3 Dose SC | 14 | 1.30 | (1.01, 1.68) |
| | Full Dose ID | 19 | 1.78 | (1.43, 2.21) |
| | 1/3 Dose ID | 19 | 1.97 | (1.59, 2.45) |
| | 1/10 Dose ID | 21 | 1.53 | (1.25, 1.89) |
| | 1/27 Dose ID | 15 | 1.19 | (0.93, 1.54) |

†205.86 Ab/mL is the median of the baseline gpELISA titers.

FIG.9

Summary of Fold−Rise From Baseline in VZV IFN−γ ELISPOT at Week 6 Post−Vaccination

| Treatment Group | n | Point Estimate (GMFR) | 90% CI |
|---|---|---|---|
| Full Dose SC | 52 | 1.51 | (1.24, 1.84) |
| 1/3 Dose SC | 34 | 1.71 | (1.34, 2.18) |
| Full Dose ID | 34 | 1.84 | (1.45, 2.35) |
| 1/3 Dose ID | 35 | 1.91 | (1.50, 2.43) |
| 1/10 Dose ID | 34 | 1.43 | (1.13, 1.82) |
| 1/27 Dose ID | 34 | 1.14 | (0.89, 1.45) |

FIG.11A

Summary of VZV IFN−γ ELISPOT Geometric Mean Counts at Baseline and Week 6 Post−Vaccination

| Visit | Treatment Group | N | Point Estimate (GMC) | 90% CI |
|---|---|---|---|---|
| Day 1 | Full dose V211 SC | 52 | 73.94 | (56.45, 96.86) |
| Day 1 | 1/3 dose V211 SC | 34 | 49.27 | (30.49, 79.61) |
| Day 1 | Full dose V211 ID | 33 | 38.56 | (27.78, 53.52) |
| Day 1 | 1/3 dose V211 ID | 35 | 37.06 | (23.95, 57.33) |
| Day 1 | 1/10 dose V211 ID | 34 | 45.16 | (29.92, 68.18) |
| Day 1 | 1/27 dose V211 ID | 34 | 56.69 | (35.32, 90.99) |
| Day 42 | Full dose V211 SC | 51 | 98.87 | (74.70, 130.86) |
| Day 42 | 1/3 dose V211 SC | 33 | 93.19 | (74.67, 116.32) |
| Day 42 | Full dose V211 ID | 34 | 75.21 | (54.34, 104.11) |
| Day 42 | 1/3 dose V211 ID | 34 | 77.34 | (54.77, 109.21) |
| Day 42 | 1/10 dose V211 ID | 34 | 66.98 | (43.92, 102.15) |
| Day 42 | 1/27 dose V211 ID | 33 | 60.82 | (37.59, 98.40) |

FIG.11B

Summary of Fold-Rise From Baseline in VZV IFN-γ ELISPOT at Week 6 Post-Vaccination by Age Stratum

| Age Stratum | Treatment Group | n | Point Estimate (GMFR) | 90% CI |
|---|---|---|---|---|
| 50 to 59 Years | Full Dose SC | 26 | 1.40 | (1.03, 1.91) |
| | 1/3 Dose SC | 16 | 1.68 | (1.15, 2.45) |
| | Full Dose ID | 17 | 1.77 | (1.22, 2.58) |
| | 1/3 Dose ID | 16 | 1.83 | (1.25, 2.67) |
| | 1/10 Dose ID | 16 | 1.51 | (1.03, 2.20) |
| | 1/27 Dose ID | 16 | 0.96 | (0.66, 1.40) |
| ≥60 Years | Full Dose SC | 26 | 1.59 | (1.23, 2.06) |
| | 1/3 Dose SC | 18 | 1.66 | (1.21, 2.27) |
| | Full Dose ID | 17 | 1.85 | (1.35, 2.54) |
| | 1/3 Dose ID | 19 | 2.11 | (1.55, 2.87) |
| | 1/10 Dose ID | 18 | 1.41 | (1.04, 1.92) |
| | 1/27 Dose ID | 18 | 1.30 | (0.95, 1.78) |

FIG.11C

Summary of VZV IFN-γ ELISPOT Geometric Mean Counts T at Baseline and Week 6 Post-Vaccination By Age Stratum

| Age Stratum | Visit | Treatment Group | n | Point Estimate (GMC) | 90% CI |
|---|---|---|---|---|---|
| 50 to 59 Years | Day 1 | Full dose V211 SC | 26 | 74.85 | (55.77, 100.45) |
| | Day 1 | 1/3 dose V211 SC | 16 | 48.52 | (25.44, 92.54) |
| | Day 1 | Full dose V211 ID | 16 | 53.19 | (33.51, 84.42) |
| | Day 1 | 1/3 dose V211 ID | 16 | 78.04 | (54.58, 111.57) |
| | Day 1 | 1/10 dose V211 ID | 16 | 70.58 | (40.93, 121.71) |
| | Day 1 | 1/27 dose V211 ID | 16 | 57.89 | (27.67, 121.15) |
| | Day 42 | Full dose V211 SC | 25 | 98.91 | (70.75, 138.26) |
| | Day 42 | 1/3 dose V211 SC | 16 | 91.15 | (63.93, 129.97) |
| | Day 42 | Full dose V211 ID | 17 | 97.34 | (60.86, 155.68) |
| | Day 42 | 1/3 dose V211 ID | 16 | 130.22 | (94.61, 179.22) |
| | Day 42 | 1/10 dose V211 ID | 16 | 101.55 | (58.78, 175.44) |
| | Day 42 | 1/27 dose V211 ID | 16 | 57.77 | (27.28, 122.32) |
| ≥60 Years | Day 1 | Full dose V211 SC | 26 | 73.05 | (45.57, 117.09) |
| | Day 1 | 1/3 dose V211 SC | 18 | 49.94 | (23.48, 106.24) |
| | Day 1 | Full dose V211 ID | 17 | 28.49 | (17.80, 45.58) |
| | Day 1 | 1/3 dose V211 ID | 19 | 19.79 | (10.01, 39.15) |
| | Day 1 | 1/10 dose V211 ID | 18 | 30.37 | (16.55, 55.72) |
| | Day 1 | 1/27 dose V211 ID | 18 | 55.64 | (28.53, 108.53) |
| | Day 42 | Full dose V211 SC | 26 | 98.84 | (62.04, 157.48) |
| | Day 42 | 1/3 dose V211 SC | 17 | 95.16 | (70.23, 128.94) |
| | Day 42 | Full dose V211 ID | 17 | 58.12 | (36.43, 92.71) |
| | Day 42 | 1/3 dose V211 ID | 18 | 48.67 | (28.11, 84.27) |
| | Day 42 | 1/10 dose V211 ID | 18 | 46.27 | (24.44, 87.59) |
| | Day 42 | 1/27 dose V211 ID | 17 | 63.83 | (32.36, 125.92) |
| n is the number of subjects contributing to the analysis. | | | | | |

FIG. 11D

Preliminary Subjects with Injection Site Adverse Event (Days 1 to 5 after vaccination)

| | Full SC n (%) | 1/3 SC n (%) | Full ID n (%) | 1/3 ID n (%) | 1/10 ID n (%) | 1/27 ID n (%) | Placebo n (%) |
|---|---|---|---|---|---|---|---|
| Subjects in Population | 52 | 34 | 34 | 35 | 34 | 34 | 39 |
| With one or more Injection Site AEs | 27 (51.9) | 7 (20.6) | 27 (79.4) | 22 (62.9) | 19 (55.9) | 19 (55.9) | 5 (12.8) |
| **General Disorders and administration site conditions** | | | | | | | |
| Injection site anaesthesia | 0 (0) | 0 (0) | 0 (0) | 1 (2.9) | 0 (0) | 0 (0) | 0 (0) |
| Injection site erythema | 16 (30.8) | 5 (14.7) | 26 (76.5) | 20 (57.1) | 16 (47.1) | 18 (52.9) | 4 (10.3) |
| Injection site haematoma | 2 (3.8) | 0 (0) | 0 (0) | 0 (0) | 0 (0) | 0 (0) | 0 (0) |
| Injection site induration | 5 (9.6) | 2 (5.9) | 12 (35.3) | 12 (34.3) | 11 (32.4) | 10 (29.4) | 1 (2.6) |
| Injection site pain | 15 (28.8) | 5 (14.7) | 8 (23.5) | 9 (25.7) | 5 (14.7) | 6 (17.6) | 0 (0) |
| Injection site pruritus | 1 (1.9) | 2 (5.9) | 3 (8.8) | 3 (8.6) | 1 (2.9) | 1 (2.9) | 0 (0) |
| Injection site rash | 1 (1.9) | 0 (0) | 0 (0) | 0 (0) | 0 (0) | 0 (0) | 0 (0) |
| Injection site scab | 0 (0) | 0 (0) | 1 (2.9) | 0 (0) | 0 (0) | 0 (0) | 0 (0) |
| Injection site swelling | 13 (25) | 4 (11.8) | 13 (38.2) | 8 (22.9) | 6 (17.6) | 7 (20.6) | 2 (5.1) |

FIG. 12

METHODS OF IMMUNIZATION WITH VARICELLA ZOSTER VIRUS ANTIGEN

CROSS-REFERENCE TO RELATED APPLICATIONS

This application is a § 371 National Stage Application of PCT/US2014/053657, international filing date of Sep. 2, 2014, which claims the benefit of U.S. Provisional Application Ser. No. 61/873,858, filed Sep. 5, 2013, which is hereby, incorporated by reference in its entirety.

FIELD OF THE INVENTION

The invention relates to methods of administration of a varicella zoster virus (VZV) vaccine to the epidermis or dermis of the skin to prevent or to reduce the likelihood of infection with VZV, or reactivation of latent VZV infection, and/or the clinical manifestations thereof.

BACKGROUND OF THE INVENTION

Primary infection with varicella zoster virus (VZV) causes chicken pox, usually in children and young adults. Chicken pox is a highly contagious disease characterized by a vesicular skin rash that can be severe, most commonly in adult males, or associated with serious complications in pregnant women and immunocompromised individuals. A live attenuated varicella virus vaccine (VARIVAX™, Merck, Whitehouse Station, N.J.) prepared from the Oka/Merck attenuated strain of varicella is available for the prevention of chicken pox in individuals 12 months of age and older. The viral strain in VARIVAX™ was initially isolated from a child infected with varicella and attenuated through serial passage in embryonic guinea pig cell cultures, followed by propagation in human diploid cell cultures (WI-38 and MRC-5). VARIVAX™ induces both humoral and cell-mediated immunity in vaccinated individuals.

Although clinical manifestations of chicken pox typically resolve without medical intervention within a short period of time, the VZV can remain latent in sensory neurons for many years following infection. Reactivation and replication of latent VZV, often decades later, can lead to herpes zoster (HZ), commonly known as shingles, a unilateral, painful rash that is generally limited to a single dermatome. Such VZV reactivation correlates with a decline in cell-mediated immunity, which occurs in the elderly or those who are immunocompromised (Weinberg et al., *Journal of Infectious Diseases* (2009) 200: 1068-77; Oxman et al., *New England Journal of Medicine* 22: 2271-84 (2005)). In some patients, pain associated with HZ can persist for months or even years after the HZ rash has healed, a complication referred to as post-herpetic neuralgia (PHN). Opthalmic zoster may also be associated with HZ, as well as other neurological complications.

A live attenuated vaccine (ZOSTAVAX®, Merck, Whitehouse Station, N.J.) is currently available for the prevention of herpes zoster in healthy individuals aged 50 or over (U.S. Pat. Nos. 6,214,354 and 5,997,880; G. M. Keating, *Drugs* DOI 10.1007/s40265-013-0088-1 (2013)). This vaccine has markedly reduced the adverse impacts of HZ in immunocompetent patient populations by boosting cell-mediated immunity to VZV (Oxman, M N, *Clin. Infect. Dis.* (2010) 51(2):197-213; Sanford and Keating, *Drugs Aging* (2010) 27(2):159-76; Oxman et al., *N Engl. J. Med.* (2005) 352: 2271-83). Results of the Shingles Prevention Study (SPS) indicate that in individuals≥60 years of age, ZOSTAVAX™ reduced the incidence of HZ by 51%, as well as HZ-associated pain, including PHN in immunocompetent adults 60 years of age or older (Oxman et al. 2005, supra). In adults 50-59 years of age, ZOSTAVAX™ reduced the incidence of HZ by 69.8%. Further reductions in the rate of HZ, particularly in the advanced elderly, are needed.

Despite the successful reduction of burden of illness associated with VZV by live attenuated vaccines, there remains an interest in development of additional VZV vaccines for different patient populations or different methods of administration, which may increase the immune response against VZV. The boost in vaccine-induced CMI varies with age of the recipient and may gradually decline over time (M. J. Levin, *Current Opinion in Immunology* 24: 494-500 (2012)). Thus, new methods of immunization, such as addition of further vaccine doses to the treatment regimen and/or use of higher dosages are being tested to increase CMI and/or duration of protection (Levin, supra).

SUMMARY OF THE INVENTION

The present invention relates to a method of vaccinating a patient against varicella zoster virus (VZV) infection or reactivation of latent VZV infection comprising administering an effective amount of a live attenuated VZV vaccine to the epidermis or the shallow dermis of the patient's skin at a depth of between about 100 and about 700 microns from the surface of the skin.

In embodiments of the invention, the patient was previously infected with VZV and is at risk of developing herpes zoster (HZ). Said methods are useful for reducing the likelihood of or preventing reactivation of latent VZV or development of HZ or complications thereof, such as PHN.

In alternative embodiments of this aspect of the invention, the patient was not previously infected with VZV and is at risk of developing chicken pox. Said embodiments are useful for preventing chicken pox or reducing the severity or duration thereof.

The invention also relates to the use of a live attenuated VZV vaccine for vaccinating a patient against VZV through shallow intradermal delivery, in accordance with the methods of the invention.

Also provided by the invention is an intradermal delivery device comprising one or more needles for penetrating the skin and a live attenuated VZV vaccine, wherein the device is adapted for shallow intradermal delivery.

As used throughout the specification and in the appended claims, the singular forms "a," "an," and "the" include the plural reference unless the context clearly dictates otherwise.

As used throughout the specification and appended claims, the following definitions and abbreviations apply:

The term "vaccinating" refers to therapeutic, or prophylactic or preventative treatment measures. Individuals in need of treatment include individuals who are "at risk" for VZV infection, VZV reactivation, or any clinical manifestations of VZV infection, as discussed more fully below.

The term "at risk" includes (1) individuals at risk for becoming exposed to VZV for the first time, particularly children, said individuals being at risk for developing chicken pox, and (2) individuals who have previously been infected with VZV (e.g. those who previously had chicken pox, those who previously were infected with varicella sub-clinically, or those who previously received a live varicella vaccine) and are at risk for developing herpes zoster, as dictated by the context. Individuals previously infected with varicella are at risk for developing a reactivation of a latent varicella infection. Individuals who are particularly at-risk for developing herpes zoster include individuals who are elderly or immunocompromised. The incidence of HZ increases with age, which correlates with declining cell-mediated immunity to VZV. Thus, in some embodiments of the invention, individuals "at risk" for developing herpes zoster are 50 years of age or older. In alternative embodiments, those "at risk" are 40 years of age or older, 45 years of age or older, 55 years of age or older, 60 years of age or older, 65 years of age or older, 70 years of age or older, 75 years of age or older, or 80 years of age or older.

Vaccinating a patient utilizing the methods of the invention includes one or more of the following: inducing/increasing an immune response against VZV in the patient, preventing, ameliorating, abrogating, or reducing the likelihood of the clinical manifestations of VZV infections in patients who have been infected with VZV, preventing or reducing the likelihood of developing chicken pox, herpes zoster, post-herpetic neuralgia and/or other disease or complication associated with VZV infection, reducing the severity or duration of the clinical symptoms of VZV infection and/or other disease or complication associated with VZV infection, and preventing or reducing the likelihood of VZV infection in individuals who have not been previously exposed to VZV or preventing or reducing the likelihood of reactivation of latent varicella infection in those already infected with VZV.

The term "therapeutically effective amount" or "effective amount" means sufficient vaccine composition is introduced to a patient through the vaccination methods of the invention to produce a desired effect, including, but not limited to those provided above. Indicators of effective amount may include one or more of the following: increase in VZV specific responder cell frequency, elevation in anti-VZV cytotoxic T-cells (as measured by elevation of VZV specific CD8+ cells), elevation of anti-VZV helper T-cells (as measured by elevation of VZV-specific CD4+ cells), increase in the level of anti-VZV specific antibodies. See U.S. Pat. No. 5,997,880. One skilled in the art recognizes that this level may vary.

The term "shallow intradermal administration" or "shallow ID administration" or "shallow ID delivery" refers to administration or delivery of a VZV vaccine to the epidermis or shallow dermis of the skin. Shallow ID delivery refers to administration of a vaccine to the individual's skin at a depth of between about 100 and about 700 microns from the surface of the skin. By use of the term "shallow ID delivery" it is not intended that a portion of the vaccine dose cannot be delivered outside of the desired range, e.g. a small portion of the vaccine may be released into the stratum coreum when the needle(s) of the ID delivery device are removed from the skin and/or a portion of a vaccine dose may migrate deeper into the skin after the initial delivery. Rather, the term refers to the initial delivery of most of a vaccine dose within the desired range.

The term "immune response" refers to a cell-mediated (T-cell) immune response and/or an antibody (B-cell) response.

The term "patient" refers to a human being that is to receive a VZV vaccine in accordance with the methods described herein. As defined herein, a "patient" includes those already infected with VZV, either through natural infection or vaccination, or those that may subsequently be exposed.

The following abbreviations are used herein and have the following meanings: AEs=adverse events, CI=confidence interval, DOD=delta optical density, ELISPOT=enzyme-linked immunospot, HSV=herpes simplex virus, HZ=herpes zoster (shingles), GMC=geometric mean counts, GMFR=Geometric Mean Fold Rise, gp=glycoprotein, gpELISA=glycoprotein enzyme-linked immunosorbent assay, ID=intradermal, IFN-γ=interferon gamma, OD=optical density, PCR=polymerase chain reaction, PBMC=peripheral blood mononuclear cells, PFU=plaque forming unit, PHN+ post-herpetic neuralgia, SFCs=spot forming cells, SC=subcutaneous, TCC=tissue culture control, V211=ZOSTAVAX™, VAS=visual analog scale, VRC=vaccine report card, VZV=varicella zoster virus.

BRIEF DESCRIPTION OF THE DRAWINGS

FIG. 2 provides the preliminary disposition of study subjects, as described in Example 3.

FIG. 3 summarizes the characteristics of the study subjects of the trial described in Example 3.

FIG. 6 provides a summary of fold-rise from baseline in VZV antibody responses measured by gpELISA at week 6 post-vaccination. Estimates are least squares means based on a constrained longitudinal data analysis model with unstructured covariance.

FIG. 7 provides a preliminary summary of baseline titer and VZV antibody responses at week 6 post-vaccination measured by gpELISA. Estimates were back-transformed after a log transformation.

FIG. 8 is a preliminary summary of fold-rise from baseline in VZV antibody responses measured by gpELISA at week 6 post-vaccination by age stratum. Estimates are least squares means based on a constrained longitudinal data analysis model with unstructured covariance.

FIG. 9 provides a preliminary summary of fold-rise from baseline in VZV antibody responses measured by gpELISA at week 6 post-vaccination by baseline gpELISA titer. Estimates are least squares means based on a constrained longitudinal data analysis model with unstructured covariance.

FIG. 11A provides a summary of fold-rise from baseline in VZV IFN-γ ELISPOT at week 6 post-vaccination. Estimates are least squares means based on a constrained longitudinal data analysis model with unstructured covariance. n is the number of subjects contributing to the analysis. FIG. 11B provides a summary of ELISPOT Geometric Mean Counts (GMC) at baseline and week 6 post-vaccination by treatment group. There was considerable variability in the baseline GMCs with the full dose SC group having the highest GMC. FIG. 11C shows a summary of the fold-rise from baseline in VZV antibody responses measured by ELISPOT at Week 6 post-vaccination by treatment group and age stratum. Estimates are least squares means based on a constrained longitudinal data analysis model with unstructured covariance. FIG. 11D provides a summary of ELISPOT GMC at baseline and Week 6 post-vaccination by treatment group and age stratum.

FIG. 12 provides a summary of injection site adverse events for subjects in the study population. A subset of subjects across all dose groups were randomized to receive a saline (placebo) injection with the MicronJet™ (Nanopass Technologies, ltd.) needle in the arm opposite from ZOSTAVAX™ administration to provide a control for the safety of the device.

DETAILED DESCRIPTION OF THE INVENTION

Figure 1A:
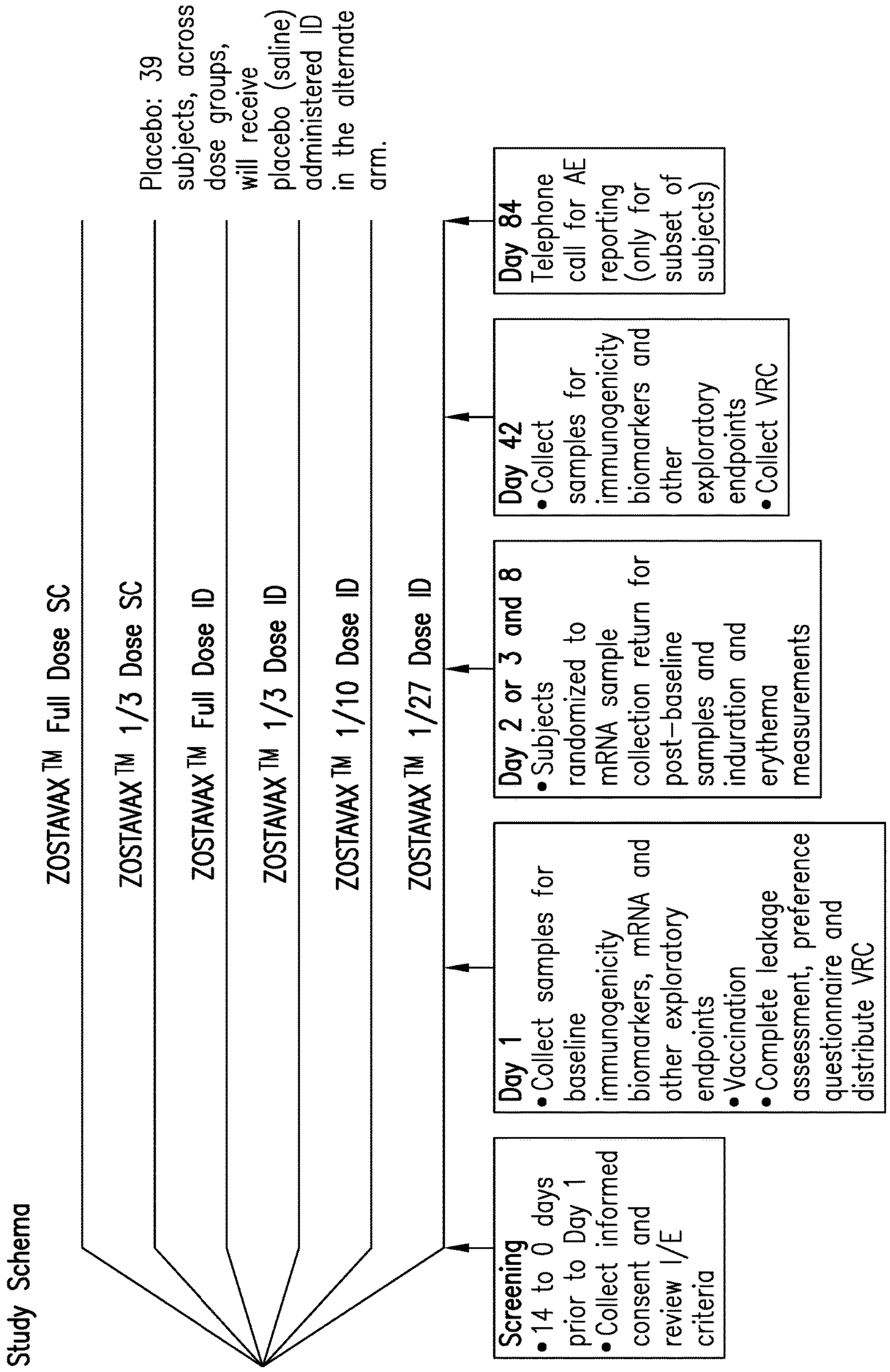
FIG. 1A provides a schema of a clinical trial of volunteers aged 50 or greater, who received dosages of ZOSTAVAX™ either subcutaneously with a needle or through shallow intradermal administration using the NanoPass MicronJet600™ needle hub.

The present invention relates to a method for vaccinating against varicella zoster virus ("VZV"), which is useful for (1A) preventing herpes zoster ("HZ"), (1B) reducing the likelihood of HZ, (1C) reducing the severity or duration of HZ, or (1D) preventing, or reducing the likelihood, severity or duration of clinical manifestations of VZV and/or complications associated with HZ, such as post-herpetic neuralgia ("PHN," e.g. reducing the severity of PHN to a period of less than one month following development of HZ), in an individual at risk of developing HZ; or (1E) preventing or reducing the likelihood of reactivation of latent VZV in an individual previously infected with VZV, or (1F) inducing a protective immune response against VZV in an individual previously infected with VZV, or (1G) inducing the elevation of anti-VZV immune responses (e.g. increasing the cell-mediated immunity) in an individual previously infected with VZV; said method comprising: administering an effective amount of a live attenuated VZV vaccine to the epidermis or the shallow dermis of the individual's skin at a depth of between about 100 and about 700 microns from the surface of the skin. These methods are collectively referred to herein as "methods for prevention of herpes zoster".

The vaccination methods described herein are useful for increasing the cell-mediated immunity to VZV in a patient previously infected with VZV, either naturally or through vaccination with a live attenuated VZV vaccine, thereby reducing the risk of reactivation of latent VZV infection. Delivery of VZV vaccine though the methods described herein elicits a robust immune response, including an antibody response as well as a T-cell dependent response.

The invention also relates to a method of vaccinating against VZV in a patient not previously infected with VZV. Such methods are useful for (2A) preventing, reducing the likelihood of, or reducing the severity or duration of chicken pox or complications thereof, or (2B) preventing or reducing the likelihood of VZV infection in an individual not previously infected with VZV, (2C) inducing an immune response against VZV in an individual not previously infected with VZV; said method comprising: administering an effective amount of a live attenuated VZV vaccine to the epidermis or the dermis of the individual's skin at a depth of between about 100 and about 700 microns from the surface of the skin. These methods are collectively referred to herein as "methods for the prevention of chicken pox".

Intradermal delivery of vaccines was previously tested with different vaccines, including inactivated influenza, attenuated, live measles virus, cholera, rabies, hepatitis B and inactivated polio virus. Although evidence of dose-sparing was shown in some instances, few clinical trials characterize the dose response adequately to know whether lower amounts of vaccine delivered conventionally would also provide similar levels of immunogenicity. Equivalent-dose ID delivery of influenza vaccines improve immunogenicity over standard injection (Holland et al. Intradermal influenza vaccine administered using a new microinjection system produces superior immunogenicity in elderly adults: a randomized controlled trial. *J Infect Dis.* 198(5):650-8 (2008); Arnou et al. Intradermal influenza vaccine for older adults: a randomized controlled multicenter phase III study. *Vaccine* 27(52):7304-12 (2009)). However, previous studies of ID delivery of varicella-containing vaccines did not support the benefits of ID delivery relative to SC vaccination (delivered to the subcutaneous tissue below the skin), as discussed, infra.

Intracutaneous vaccination was tested with a varicella vaccine by Ferencz in 1946 (Ferencz, Nepegeszsegugy, 8:497). This study was described by Boda (Active Immunization against Varicella. *Lancet* 1: 570 (1975)), who indicated that Ferencz utilized a vaccination process called "varicellisation," in which clear vesicular fluid obtained from varicella-infected patients was diluted (20-fold) and given intracutaneously to prevent chicken pox. A study was later conducted by Boda and colleagues (Active immunization of children exposed to varicella infection in a hospital ward using live attenuated varicella vaccine given subcutaneously or intracutaneously. *Acta Paediatrica Hungarica,* 27 (3): 247-252 (1986)) comparing the subcutaneous and intracutaneous route of vaccination against varicella disease in children. It was likely that the Mantoux technique was utilized for transcutaneous delivery in this study since that was the accepted practice at that time. Use of the Mantoux technique delivers vaccine to the reticular dermis of the skin at a depth of approximately 3 mm (~3000 microns), due to the use of a beveled needle. For ID injection using the Mantoux technique, the entire bevel of the needle is inserted by a technician into the skin, resulting in delivery below the epidermis and shallow dermis of the skin. See *Mantoux Tuberculosis Skin Test Facilitator Guide* (Centers for Disease Control and Prevention, Division of Tuberculosis Elimination, Atlanta, Ga.).

Boda and colleagues (1986, supra) noted that although a satisfactory antibody response was obtained in children one month following immunization, the results in the subcutaneous group were somewhat better (Boda, 1986). Additionally, in patients that received the vaccination intracutaneously, two cases of abortive varicella occurred, whereas none were observed in the subcutaneous group. Furthermore, intracutaneous vaccination in children resulted in fewer seroconversions when compared to subcutaneous vaccination (10 of 13 and 12 of 13 seroconversions, respectively). Boda et al. (supra) indicated that intracutaneous vaccination appeared less effective than subcutaneous vaccination in children. These clinical studies suggested that subcutaneous vaccination was superior to intracutaneous vaccination with varicella. However, shallow ID delivery of VZV vaccines was not previously tested. Thus, the mode of administration of approved VZV vaccines (VARIVAX™ (Merck) and ZOSTAVAX™ (Merck)) remains via subcutaneous injection through the current time.

We have shown herein that, surprisingly, delivery of a VZV vaccine (ZOSTAVAX™, Merck, Whitehouse Station, N.J.) to the shallow skin (epidermis and shallow dermis) resulted in greater immunogenicity than SC immunization, as measured by varicella specific antibodies, in adults 50 years of age and older. Administration to the shallow portion of the skin was accomplished through the use of a modern delivery device that targets this depth (MicronJet™, Nanopass Technologies, Ltd., Nes Ziona, Israel). In previous studies, gpELISA and VZV IFN-γ ELISPOT were examined in individuals who experienced HZ disease to model immunological correlates of disease protection. In subjects 60 years of age and older, the greatest extent of vaccine effect was explained by gpELISA titer and fold rises at 6 weeks after vaccination (Oxman et al., 2005, supra). Thus, evidence suggests gpELISA is an indicator of HZ protection. It is shown herein that intracutaneous (intradermal) administration to the shallow skin (epidermis and shallow dermis) is superior to subcutaneous delivery with a varicella-containing vaccine, ZOSTAVAX™, based on antibody titers by gpELISA (see Example 8).

Previous studies have also shown that, VZV IFN-γ ELISPOT data correlates with protection against HZ, albeit to a lesser extent than that of antibody titers. In the current study, a T-cell immune response was also observed in individuals who received the VZV vaccine through shallow ID administration. It is also shown herein that the point estimates for ELISPOT GMFR were higher in individuals that received a full or ⅓ dose of ZOSTAVAX™ via shallow intradermal delivery relative to those that received the vaccine through conventional SC delivery (see EXAMPLE 8).

This invention demonstrates that shallow intradermal delivery is dose sparing, with reduced amounts of vaccine required for an equivalent immune response when delivered ID relative to SC administration (e.g. $1/10^{th}$ dose of ZOSTAVAX™ administered intradermally resulted in an antibody titer that was higher than that generated by subcutaneous administration of a full dose). We have also shown that the titer rise, as measured by gpELISA, was consistent with a dose response with shallow ID vaccination, unlike previous studies with SC vaccination (Oxman et al., A Vaccine to Prevent Herpes Zoster and Postherpetic Neuralgia in Older Adults. *New England Journal Medicine* 352: 2271-2284 (2005)).

Without wishing to be bound by theory, it is believed that superior results obtained with the methods described herein utilizing shallow ID delivery were due to direct administration of the vaccine to the shallow skin (i.e. epidermis and shallow dermis). The narrow layer beneath the skin surface contains a higher density of potent antigen presenting dendritic cells (DC) and a wider variety of DC than deeper layers of skin (e.g. Langerhans cells are present in the epidermis, but not the dermis of the skin). It is believed that virulent VZV replicates in the skin upon ID delivery and infects skin derived dendritic cells. It was recently shown that VZV interferes with signaling through toll-like receptor-2 (TLR-2), the receptor for lipoteichoic acid and zymosan, which subverts dendritic cell promotion of a Th1 response. This virulence mechanism is proposed to be lost during attenuation of the vaccine virus (Gutzeit et al. Identification of an important immunological difference between virulent varicella-zoster virus and its avirulent vaccine: viral disruption of dendritic cell instruction. *J. Immunol.* 185(1): 488-97 (2010)). Infection with OKA strain permits maturation of DC and the release of IFN-γ and IL-12, potent drivers of Th1 lymphocyte maturation. Therefore, in accordance with the present invention, shallow ID delivery of ZOSTAVAX™ to skin dendritic cells may improve cell mediated immunity.

We have also shown herein that shallow ID injection to the epidermis and shallow dermis of the skin was not associated with any vaccine-related adverse events, although local injection site reactions were more frequent with ID injection with the MicronJet™ (Nanopass Technologies Ltd.) needle compared to SC injection with a conventional needle. This is consistent with results from studies with shallow ID vaccination of influenza vaccine, wherein greater frequency and severity of transient, local injection site reactions were observed (Van Damme et al. Safety and efficacy of a novel microneedle device for dose sparing intradermal influenza vaccination in healthy adults. *Vaccine* 27(3): 454-9 (2009); Belshe et al. Comparative immunogenicity of trivalent influenza vaccine administered by intradermal or intramuscular route in healthy adults. *Vaccine* 25(37-38):6755-63 (2007)). It is not known whether the greater apparent increase in injection site reactions reflects a true increase in inflammation or is merely a reflection of the superficial site of application that makes signs of inflammation more noticeable.

In accordance with the methods of the invention, an effective amount of live attenuated VZV vaccine is delivered to the shallow skin of a patient, depending on the desired clinical outcome and patient population. The amount of live attenuated VZV vaccine to be delivered may be measured in terms of infectivity titer or infectious units. Infectious units are routinely estimated by determining the amount of plaque production in cell culture, referred to as plaque forming units (PFUs). Exemplary effective amounts of live attenuated VZV vaccines are disclosed herein. The PFU's of the live attenuated vaccine may be determined using, for example, a varicella plaque assay such as the assay described in Krah et al. (*J. Virol. Methods* (1990) 27: 319-26) and further described in Example 1 of WO2012/018973. The infectivity of a sample may also be confirmed by an immunostaining method, as described in Example 1 of WO2012/0189731.

A live attenuated VZV strain can be used in the methods described herein, including an attenuated VZV strain known in the art such as the Oka strain, as described in U.S. Pat. No. 3,985,615. The Oka strain was originally obtained from a healthy boy with a natural varicella infection and passaged in human embryonic lung cells. It was adapted to growth in guinea pig embryo cell cultures and human diploid lung fibroblast cell cultures (e. g., MRC-5 cells). In preferred embodiments of the compositions and methods described herein, the VZV is an Oka strain (a.k.a. "pOka," "parental Oka", or "Oka/Biken") or an Oka strain derivative, such as the Oka/Merck (a.k.a. Oka-$V_{Merck}$) and Oka/GSK (a.k.a. Oka/RIT, Oka-$V_{GSK}$) VZV strains (See Tillieux et al., *J. Virol.* 82: 11023 (2008); Gomi et al., *J. Virol.* 76: 11447 (2002); and Kanda et al. *Vaccine* 29: 3293 (2011)). An "Oka strain derivative," as used herein, is a strain that is obtained by a process of further passaging the Oka strain in an appropriate cell type in order to sufficiently attenuate the strain so as to be useful, for example, as a live attenuated VZV vaccine. Wild-type VZV strains can also be obtained from a variety of sources, such as from an individual infected with VZV, and attenuated by different techniques, including methods known in the art such as through serial passage on tissue culture or through more defined genetic manipulations.

The live attenuated VZV vaccine is delivered to the dermis or shallow epidermis of the individual's skin at a depth of about 100 to about 700 microns from the surface of the skin. In alternative embodiments, shallow ID delivery comprises delivery at a depth of about 100 microns, about 200 microns, about 300 microns, about 400 microns, about 500 microns, about 600 microns or about 700 microns. In additional embodiments, shallow ID delivery comprises delivery to a depth of about 100 to about 600 microns, about 100 to about 500 microns, about 100 to about 400 microns, about 200 to about 700 microns, about 200 to about 600 microns, about 200 to about 500 microns, about 300 to about 700 microns, about 300 to about 600 microns, about 300 to about 500 microns, about 400 to about 700 microns, about 400 to about 700 microns, or about 400 to about 600 microns.

In the methods of the invention, shallow intradermal delivery is achieved through the use of an intradermal delivery device comprising one or more needles for penetrating the skin; wherein the device is adapted for shallow intradermal delivery. Said intradermal delivery device can be an apparatus that is capable of delivering vaccine to the desired depth of the skin. For example, the ID delivery device may comprise a pre-filled syringe comprising liquid VZV vaccine for delivery to the desired depth through a single or multiple hollow needle(s). Alternatively, the device may comprise multiple, solid needles, such as a patch, which are coated with dried VZV vaccine. In either case, when the device is used for the methods described herein, the resulting depth of delivery should be to the epidermis or shallow dermis of the skin. Depth of delivery can be controlled, e.g., by varying the length of the one or more needles of the intradermal delivery device. For example, an ID delivery device equipped with one or more needles that are 600 microns in length (e.g. the MicronJet™ ID device), would be capable of delivering vaccine to the desired depth and targeting the antigen-presenting dendritic cells in the shallow skin. Devices useful for the methods of the invention include, for example, devices described in WO 2010/067319. In exemplary embodiments of the invention, the intradermal delivery device is a MicronJet600™ needle hub and syringe (Nanopass Technologies Ltd., Nes Ziona, Israel).

The needle(s) of the intradermal delivery device may be made of a material that is safe for human use and is shaped to penetrate the skin. In embodiments of the invention, the needle is made of silicon, metal, such as stainless steel, or a polymer. Additionally, materials known for use in micro electro mechanical systems may be used for the needle as long as said material is safe for use with human therapeutic methods. Advantageously, the needle should be shaped in a way that allows the piercing of the stratum corneum, or top layer of the skin. For example, the tip of the needle can be cut into a bevel to readily allow penetration of the skin. Additionally, it may be advantageous in some instances to use needles that at least partially dissolve upon penetrating the patient's skin.

Accordingly, the invention also provides an intradermal delivery device adapted for shallow intradermal delivery which comprises a live attenuated VZV vaccine and one or more needles for penetrating the skin. The one or more needles of the ID delivery device are made of silicon, stainless steel, a polymer, a biodegradable material or other material that is safe for human use and shaped for penetration of the skin.

In some embodiments of this aspect of the invention, the device the live attenuated VZV vaccine is liquid and the one or more needles are hollow. In alternative embodiments, the live attenuated VZV vaccine is dried and the one or more needles are solid.

Methods for the Prevention of Herpes Zoster:

Methods 1(A)-1(G) comprise shallow intradermal administration of a live attenuated VZV vaccine to a patient at risk for developing HZ, i.e. a patient previously infected with VZV. In some embodiments of this aspect of the invention, the patient is 40 years of age or older, 45 years of age or older, 50 years of age or older, 55 years of age or older, 60 years of age or older, 65 years of age or older, 70 years of age or older, 75 years of age or older, or 80 years of age or older. In preferred embodiments, the patient is 50 years of age or older. In additional embodiments, the patient is from about 40 to about 90 years of age, from about 40 to about 85 years of age, from about 40 to about 80 years of age, from about 45 to about 90 years of age, from about 45 to about 85 years of age, from about 45 to about 80 years of age, from about 50 to about 90 years of age, from about 50 to about 85 years of age, from about 50 to about 80 years of age, from about 55 to about 85 years of age, from about 60 to about 85 years of age, or from about 65 to about 85 years of age.

In embodiments of the methods of the invention described above, an effective amount of vaccine comprises from about 19,000 plaque forming units (PFUs) to about 56,000 PFUs of live VZV vaccine, equivalent to a "full dose" of vaccine for SC administration. It is shown herein that use of the methods of the invention, i.e. use of shallow intradermal delivery, allows the use of lesser amounts of vaccine to achieve equivalent efficacy relative to methods comprising SC administration. To that end, in alternative embodiments of the invention, from about 9,500 PFUs to about 28,000 PFUs of live attenuated VZV vaccine is administered to the individual ("½ dose"). In further embodiments, from about 6,300 PFUs to about 18,700 PFUs of live attenuated VZV vaccine is administered to the individual ("⅓ dose"). In still further embodiments, from about 1,900 PFUs to about 5,600 PFUs of live attenuated VZV vaccine is administered to the individual ("1/10 dose"). In additional embodiments, the amount of live attenuated VZV vaccine introduced to the vaccine recipient using the methods herein is between about 700 PFU's and 2075 PFU's ("1/27 dose"). In additional embodiments, at least 18,000, at least 19,000, at least 20,000, at least 21,000, at least 22,000, at least 23,000, at least 24,000, at least 25,000, at least 26,000, at least 27,000, at least 28,000, at least 29,000, or at least 30,000 PFUs of vaccine are administered to the individual.

In additional embodiments of methods 1(A)-1(G) described herein, the live attenuated VZV vaccine is administered concomitantly with one or multiple other commonly administered 'standard of care' therapies; or with other vaccines for targeted patient populations, including, for example, a pneumococcal vaccine such as PNEUMOVAX™ 23 (PN23, Merck, Whitehouse Station, N.J.) a hepatitis B (HBV) vaccine such as RECOMBIVAX™ HB (Merck) or ENGERIX-B™ (GlaxoSmithKline Biologicals, Rixensart, Belgium) and flu vaccines. Use of the term "concomitant administration" does not require that both or all of the vaccines to be administered must be administered via ID delivery, just that a second or multiple vaccines are administered to the same patient within the same period of time (e.g. within a 24-hour period). In accordance with the methods of the invention, the VZV vaccine is delivered to the shallow skin whereas the second or multiple other vaccines may be delivered by ID delivery or by a route of administration that has been shown to be safe and effective for the particular vaccine being administered.

The timing of VZV doses using the methods described herein depends upon factors well known in the art. After the initial administration one or more additional doses may be administered if necessary to maintain and/or boost antibody titers or CMI response to VZV. In specific embodiments of the methods of prevention provided herein, the method further comprises allowing an appropriate predetermined amount of time to pass and administering to the patient one or more additional doses of the live attenuated VZV vaccine using the methods described herein. In said embodiments, one additional dose may be administered to the patient after an appropriate amount of time has passed, alternatively, two, three or four additional doses, each being administered after an appropriate amount of time has passed. One skilled in the art will realize that the amount of time between doses may vary depending on the patient population, dosage of the vaccine and/or patient compliance. In embodiments of the invention, a time period of about 1 month, about 6 months, about 1 year, about 2 years, about 5 years, about 7 years, about 10 years or about 15 years or more is allowed to pass between administrations of each dose to the patient.

It is also contemplated that a therapeutic regimen may include delivery of a live attenuated VZV vaccine to the shallow skin in accordance with the methods described herein and delivery of a second VZV vaccine, such as an inactivated VZV vaccine, through a different method of administration such as SC or intramuscular after a predetermined amount of time has passed. Such methods may be advantageous, for example, where a vaccine recipient becomes immunocompromised after the time of the initial dose of VZV vaccine and it is desired to deliver an additional VZV vaccine dose that is inactivated for safety reasons.

Methods for the Prevention of Chicken Pox:

In alternative embodiments of the methods of the invention described above (methods 2(A)-2(C)), an effective amount of vaccine which is delivered to an at-risk patient (i.e. a patient that has not been previously exposed to VZV) in accordance with the methods of the invention comprises about 1350 PFU's of live attenuated VZV vaccine or greater. In alternative embodiments, the invention comprises at least 100, at least 200, at least 300, at least 400, at least 500, at least 600, at least 700, at least 800, at least 900, at least 1000, at least 1100, at least 1200 or at least 1300 PFU's of a live attenuated VZV vaccine are administered to the individual.

Methods 2(A)-2(C) comprise shallow intradermal administration of a live attenuated VZV vaccine to a patient at risk for chicken pox, i.e. an individual not previously infected with VZV. In embodiments of this aspect of the invention, the individual is between about 12 months and 12 years of age. In additional embodiments, the individual is 12 years of age or older.

In additional embodiments of methods 2(A)-2(C) described herein, the live attenuated VZV vaccine is administered in accordance with the methods of the invention concomitantly with other commonly administered 'standard of care' therapies; or with other vaccines targeted for the same patient populations (e.g. children). For example, the live attenuated VZV vaccine may be administered concomitantly with a measles vaccine, a mumps vaccines, a rubella vaccine, an MMR combined vaccine, a poliovirus vaccine, a diphtheria vaccine, a tetanus toxoid vaccine, an acellular pertussis vaccine, a DTaP combined vaccine, a haemophilus b conjugate vaccine, a flu vaccine, or a hepatitis b vaccine.

The invention herein is also related to the use of a live attenuated VZV vaccine for a method of vaccinating a patient in accordance with the methods of the invention.

Further provided by the invention is a live attenuated VZV vaccine for use in a method of vaccinating a patient against VZV infection or VZV reactivation in accordance the methods of the invention.

All publications mentioned herein are incorporated by reference for the purpose of describing and disclosing methodologies and materials that might be used in connection with the present invention.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

Materials and Methods

Example 1

Detection of VZV Antibody Using gpELISA

The purpose of the gpELISA was to detect IgG antibody to VZV before and after vaccination with VZV-containing vaccine(s). This method was used to detect antibodies to VZV glycoprotein (gp), which have been purified from MRC-5 cells infected with the KMcC strain of VZV by lectin affinity chromatography. To determine antibody titers, the reactivity of the sera to the gp antigens from uninfected MRC-5 cells (denoted as Tissue Culture Control [TCC] wells]) was subtracted from the reactivity of the sera to the gp antigens purified from VZV-infected MRC-5 cells. The assay and the purification of the VZV gp from VZV-infected cells were as described (Keller et al. Purification of individual varicella-zoster virus (VZV) glycoproteins gpI, gpII, and gpIII and their use in ELISA for detection of VZV glycoprotein-specific antibodies. *J Virol Methods* 14(2):177-88 (1986); Wasmuth et al. Sensitive enzyme-linked immunosorbent assay for antibody to varicella-zoster virus using purified VZV glycoprotein antigen. *J Med Virol* 32(3):189-93 (1990); Provost et al. Antibody assays suitable for assessing immune responses to live varicella vaccine. *Vaccine* 9(2):111-6 (1991)). Serum sample titers as determined by gpELISA were previously shown to correlate with neutralizing antibody titers (Krah et al. Comparison of gpELISA and neutralizing antibody responses to Oka/Merck live varicella vaccine (Varivax™) in children and adults. *Vaccine* 15(1):61-4 (1997)).

For the gpELISA, VZV gp or TCC antigen were adsorbed to polystyrene microtiter wells and used as the solid phase antigen. Experimental, control, and standard curve sera were incubated in VZV gp-coated and TCC-coated wells (2 wells for each antigen). For each serum sample, a delta optical density (DOD) was calculated as the difference between the average optical density (OD) of the 2 VZV antigen wells and the average OD of the 2 TCC wells. Quantitation was obtained by comparison of sample DOD with a standard curve. Results for the assay were reported as the concentration of antibody in gpELISA units/mL.

The negative control used for this assay was an individual human serum at a dilution of 1:50, found to be negative for anti-VZV. The high-positive control was a VZV antibody-positive serum, diluted 1:500, which gave a response in the assay at the upper end of the standard curve. The low-positive control was a VZV antibody-positive serum diluted 1:50, which gave a response in the assay at the lower end of the standard curve. A VZV antibody-positive individual human serum was used to generate a standard curve.

Example 2

Measurement of Cell-Mediated Immunity by VZV IFN-γ ELISPOT

A VZV IFN-γ ELISPOT assay was performed to evaluate the cell mediated immune response to ZOSTAVAX™ after ID or SC delivery to a subject. The VZV ELISPOT assay was to detect IFN-γ secreting VZV-specific cells from PBMCs before and after vaccination with VZV-containing vaccine(s). PBMCs were isolated, frozen, and stored at a central laboratory or biorepository after collection. Results for the assay were expressed as the frequency of spot forming cells (SFCs) per million PBMCs.

The IFN-γ ELISPOT assay utilized 2 high-affinity IFN-γ specific monoclonal antibodies that were directed against different epitopes on the IFN-γ molecule. In the VZV-specific IFN-γ ELISPOT assay, $5\times10^5$ PBMCs were stimulated by VZV antigen in wells of cell culture plates that were pre-coated with one mouse monoclonal antibody to human IFN-γ. IFN-γ released by the VZV-specific T-cells then bound to the first antibody present in close proximity to the cells that produced it. After ~18 hours in culture, the cells were washed away, and a biotinylated form of the second antibody to IFN-γ was added to the wells of the plate and incubated overnight at 4° C. The plates were washed and then alkaline phosphatase-streptavidin was added to each well of the plate. After 2 hours of incubation at room temperature, the plates were washed again and a chromogenic substrate (NBT/BCIP) was added to react with the alkaline phosphatase. As a result, dark blue spots developed against the white background of the plates. The IFN-γ produced by each cell resulted in the formation of a spot on the culture plate, with the number of spots approximating the number of cells that produced IFN-γ in response to VZV antigen.

The frequency of SFCs was expressed per million input PBMCs. The results reflect the T-cell precursor frequency specific to VZV circulating in the blood at a defined time point. The source of antigen used to stimulate VZV-specific responses was a UV-inactivated virus stock of the Oka/Merck vaccine strain that was produced in MRC-5 cells. A similar preparation from uninfected MRC-5 cells was used as the negative control.

Example 3

Measurement and Recordation of Injection Site and Systemic Reactions to Vaccination A Vaccine Report Card (VRC) was distributed for the subject to record frequency and severity of local reactions to the immunization with ZOSTAVAX™ from each injection site following the injection and systemic reactions for 42 days. Subjects receiving an injection in both arms were instructed to complete injection-site reaction information for both arms. Subjects receiving more than one injection in one arm completed the VRC for each injection, provided the injection reactions were distinguishable from each other. Subjects were instructed to record daily oral temperatures and injection-site and systemic adverse experiences on the VRC from Day 1 to Day 42 post-vaccination. The VRC was used to actively prompt for local injection-site adverse experiences of redness, swelling, and pain/tenderness and for the size of local injection-site reactions of redness and swelling that occur within 5 days of vaccination. The presence of varicella/varicella-like rash and HZ/HZ-like rash was also captured on the VRC.

After 42 days, the subject returned for another visit where the VRC and post-vaccine immunogenicity biomarkers and exploratory endpoint samples were collected. After all Day 42 procedures were completed, the subject was eligible to receive ZOSTAVAX™ via the usual SC route if they had not previously been randomized to this regimen.

All subjects also completed a questionnaire assessing their injection pain and insertion pain, using a Visual Analog Scale (VAS) for each arm injected. If more than one injection was administered in one arm, the subject was instructed to complete the assessment for the injection that caused the most pain. In addition, those subjects who received an ID injection (either ZOSTAVAX™ or saline placebo) answered questions related to pain, apprehension, and preference for ID vaccination using the MicronJet600™ compared with the subject's personal current or historical experience with SC vaccination using a regular needle and syringe. The questionnaire was completed as soon as possible following the injection. The questionnaire was modeled on one previously used in a comparison of the MicronJet600™ and conventional needle (Van Damme et al. Safety and efficacy of a novel microneedle device for dose sparing intradermal influenza vaccination in healthy adults. *Vaccine* 27(3):454-9 (2009)). We expected that injection of saline was unlikely to produce zero pain as ID injection of saline would yield a brief mild pain response.

Skin induration and erythema measurements were collected from some subjects at the same time that they returned for blood collection as an objective measure of tissue inflammation shortly after vaccination with ZOSTAVAX™. These measurements were performed as a measure of cell mediated immunity and to determine if inflammation correlated with levels of immunity to VZV, particularly in those receiving ZOSTAVAX™ intradermally where the vaccine is delivered close to the skin surface. Measurements were made in the longest direction of the induration and the erythema on each injected arm using a 100 mm ruler. If two ID injection sites were visible, measurements were made using the site with the longest measurement.

Example 4

PCR Assay for VZV DNA in Lesion Specimens

The purpose of the VZV PCR assay was to detect VZV and herpes simplex virus (HSV) DNA in specimens obtained from subjects suspected of having varicella or herpes zoster (Harbecke et al., *J. Medical Virol.* 81:1310-1322 (2009)). The assay is a real-time PCR assay that uses virus-specific primers and probes to detect and discriminate among wild-type/Oka-parent VZV (VZV-WT/VZV-P), Oka-type attenuated VZV (VZV-O), and HSV DNA (HSV types 1 and 2). In the VZV PCR assay, virus-specific amplification was multiplexed with β-globin-specific primers and VIC-labeled fluorescent probe to demonstrate the presence of amplifiable host cell DNA in the clinical specimen.

The PCR assay is based on TaqMan® sequence detection chemistry utilizing an oligonucleotide probe that is labeled at the 5' end with a fluorescent reporter dye and at the 3' end with a fluorescent quencher dye. This probe sequence lies between 2 amplification primer sequences on the target DNA. When the probe is intact, the proximity of the quencher dye greatly reduces the fluorescence emitted by the reporter dye. If the target sequence is present in the PCR reaction, then the probe anneals downstream from one of the primer sites and is cleaved by the 5' nuclease activity of Taq DNA polymerase as this primer is extended. The cleavage of the probe separates the reporter dye from the quencher dye, increasing the reporter dye signal, and removes the probe from the target strand so that the overall PCR process is not inhibited. Additional reporter dye molecules are cleaved from their respective probes with each PCR cycle, resulting in an increase in fluorescence intensity proportional to the amount of amplicon produced.

Each reporter signal was normalized to an internal passive reference dye to adjust for fluorescence fluctuations. The normalized signals from the initial cycles of PCR, where there is little change in fluorescence, were used to determine the baseline fluorescence across the entire reaction plate. For consistency across assay plates, a fixed threshold value of 0.05 was assigned, which is above the baseline and within the region of exponential growth of PCR product.

Results for the assay were reported as the PCR cycle number (Ct) at which the fluorescence generated within a reaction crosses the threshold. A lower Ct value indicates a greater fluorescence in the reaction and correlates directly with a greater amount of target DNA present in the specimen. The cutoff that denotes a positive sample in the assay was a Ct value≤36.35.

Example 5

Statistical Methods

The primary endpoint of the study was the Geometric Mean Fold Rise from baseline (GMFR) in VZV-specific antibodies as measured by VZV gpELISA 6 weeks after administration of the full dose SC, ⅓ dose SC, full dose ID, ⅓ dose ID, 1/10 dose ID or 1/27 dose ID vaccination. All subjects who received the study vaccination and who had valid serology results were included in the immunogenicity summaries. The immune responses measured by gpELISA were natural log transformed prior to analysis.

For comparing the GMFR of VZV antibody titers measured by VZV gpELISA between the different vaccination groups, a constrained longitudinal data analysis (cLDA) method proposed by Liang and Zeger (Longitudunal data analysis of continuous and discrete responses for pre-post designs. Sankhya: *The Indian Journal of Statistics*, Volume 62, Series B, Pt. 1; 134-148 (2000)) was used. This model assumed a common mean across treatment groups at baseline and a different mean for each treatment at each of the post-baseline time points. The response vector consisted of the baseline natural log VZV antibody titers and the week 6 natural log VZV antibody titers measured by VZV gpELISA. Time was treated as a categorical variable so that no restriction was imposed on the trajectory of the means over time. An unstructured covariance matrix was used to model the correlation among repeated measurements. No multiplicity adjustments were made for comparisons between the different vaccination groups.

Example 6

ZOSTAVAX™ Intradermal Study Design

A. Hypothesis and Objectives

A primary objective of this study described below was to evaluate the change from baseline in the VZV-specific antibodies as measured by VZV gpELISA after administration of a single full dose of SC ZOSTAVAX™. Our hypothesis was that there would be an increase from baseline in the VZV-specific antibodies as measured by VZV gpELISA of greater than 1.4 fold at 6 weeks after administration of a single full dose of SC ZOSTAVAX™. The true GMFR was assumed to be ~2. Thus, the pre-defined statistical criterion which defined a successful induction of immune response for this trial required that the lower bound of the 90% confidence interval for the GMFR be >1.4, which was based on previous studies with SC administration of ZOSTAVAX®.

The study was also performed to estimate the dose-response relationship using full, ⅓, 1/10, and 1/27 doses of ZOSTAVAX™ administered by shallow ID vaccination and the VZV-specific GMFR as measured by VZV gpELISA and VZV IFN-γ ELISPOT and to compare the GMFRs obtained with shallow ID vaccination to those obtained with SC vaccination. The study was also performed to compare the systemic and local (i.e., injection site) safety of ZOSTAVAX™ administered by shallow ID vaccination with SC vaccination.

B. Patients

Generally healthy males or females 50 years of age or older were invited to participate. Subjects had a prior history of varicella (chickenpox) or residence in a country with endemic VZV infection for ≥30 years and were afebrile on the day of vaccination. Female subjects of reproductive potential demonstrated a serum or urine pregnancy test and agreed to remain abstinent, or use (or have their partner use) 2 acceptable methods of birth control for 3 months post-vaccination. Subjects were excluded if they had a prior history of HZ or had received any varicella vaccination, or recent exposure to systemic immunosuppressants or immune dysfunction. Subjects were also excluded if they had recently received live virus vaccinations, had untreated, active tuberculosis, or used antiviral drugs. Finally, subjects were excluded if they had immunosuppressed household members, as leakage of vaccine strain virus might theoretically be more likely with the ID route. Subjects provided informed consent.

C. Study Design

We conducted an exploratory, randomized, partially blinded, three center clinical study designed to compare safety and VZV immunogenicity when administering ZOSTAVAX™ at various doses via both shallow ID delivery, using the MicronJet600™ (NanoPass Technologies Ltd.) needle hub, and SC, using a needle and syringe (see FIG. 1A).

Healthy adults of 50 years of age or greater were randomized to one of six dose groups. The randomization was stratified by age in approximately a 1:1 ratio (50 to 59 and ≥60 years of age). Administration of ZOSTAVAX™ and placebo occurred after baseline samples were obtained. ZOSTAVAX™ was administered in the non-dominant arm and, in a subset of subjects, saline (placebo) was administered in the dominant arm with the MicronJet600™ needle to provide a control for the safety of the device in this population.

For all subjects, whether receiving shallow ID or SC administration, the site staff administering the vaccine immediately assessed leakage at each injection site. Leakage was categorized by the amount of fluid leakage, based on a visual assessment. For subjects with more than one injection, the assessment was completed for each injection site.

D. Treatment

Figure 1B:
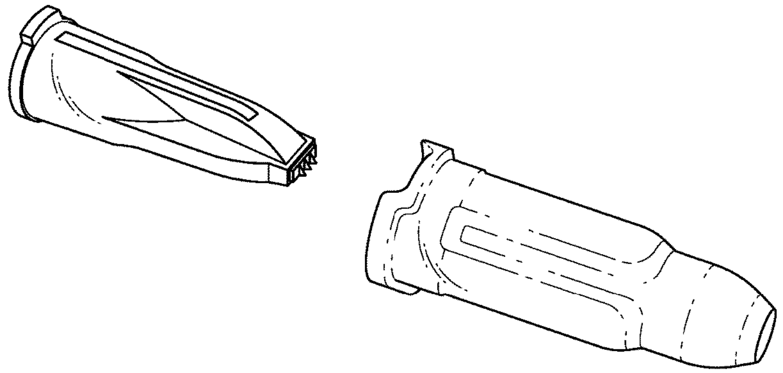
FIG. 1B provides a drawing of the NanoPass MicronJet600™ needle hub, which is adapted for shallow intradermal delivery.

Subjects received a single vaccination of 1× frozen ZOSTAVAX™. ZOSTAVAX™ is a lyophilized preparation of live, attenuated varicella-zoster virus (Oka/Merck). ZOSTAVAX™ was administered by either shallow ID injection using the NanoPass MiconJet600™ needle hub and syringe or by SC administration using a needle and syringe. All doses were administered over the deltoid muscle. The MicronJet600™ is intended to be used as a substitute for a regular needle in procedures that require intradermal injections. The MicronJet600™ is a sterile plastic device equipped with 3 microneedles, each 600 micrometers (0.6 mm) in length. This device can be mounted on a syringe instead of a standard needle (see FIG. 1B).

Subjects were randomized to receive the approved full dose of ZOSTAVAX™, or a fraction of the full dose as shown in Table 1. There were six dose groups: full dose SC, ⅓ dose SC, full dose shallow ID, ⅓ dose shallow ID, 1/10 dose shallow ID or 1/27 dose shallow ID randomized in a 1.5:1:1:1:1:1 ratio.

TABLE 1

| Subject Dosing and Administration | | | | | | |
|---|---|---|---|---|---|---|
| | Full dose V211 SC | ⅓ dose V211 SC | Full dose V211 ID | ⅓ dose V211 ID | 1/10 dose V211 ID | 1/27 dose V211 ID |
| Subjects | 51 | 34 | 34 | 34 | 34 | 34 |
| Subjects Also Receiving Placebo (Saline) ID* | 9† | 6† | 6‡ | 6† | 6† | 6† |
| Administered volume | 0.65 mL | 0.22 mL | 2 × 0.15 mL* | 0.1 mL | 0.1 mL | 0.1 mL |

*Two injections spaced approximately 5 cm apart.
A total of 39 subjects across in all SC and ID dose groups received saline placebo in the alternate arm.
†Subjects received a single ~0.1 ml ID injection of placebo (saline).
‡Subjects received two ~0.15 ml ID injections of placebo (saline).

All doses, other than the 1/27 dose ID, were reconstituted in the diluent provided for administering ZOSTAVAX™ per the guidelines provided in the package insert. The 1/27 dose shallow ID was reconstituted using sterile normal saline, as reconstituting in diluent would cause the osmolarity to be too hypotonic. In vitro tests demonstrated that the live attenuated varicella virus was viable under the conditions of use of the reconstitution instructions. gpELISA samples were collected from all subjects and analyzed during the course of the study, as described in Example 1.

Results

Example 7

Patient Accounting and Demographics

The disposition of study subjects is shown in FIG. 2. All but 2 subjects completed the study. One subject withdrew from the study while the other was lost to follow-up.

Subject demographics are provided in FIG. 3. An imbalance in the gender distribution was observed across treatment groups. There were 71% females in the 1/27 dose shallow ID group while there were approximately 60% females in the full dose SC and ⅓ dose SC groups and approximately 50% females in the full dose shallow ID, ⅓ dose shallow ID and 1/10 dose shallow ID groups. The age distribution was balanced across dose groups as expected due to the stratification by age. The race distribution was balanced across dose groups with 94% of the subjects being white. Overall 72% of the subjects were Hispanic or Latino.

Example 8

Immunogenicity of ZOSTAVAX™ Administered Intradermally or Subcutaneously.

gpELISA Results.

Comparable gpELISA GMFR was observed in ZOSTAVAX 1/27 dose shallow ID group, full dose SC group and ⅓$^{rd}$ dose SC dose. A summary of fold-rises from baseline in VZV antibody responses measured by gpELISA at 6 weeks post-vaccination is shown in FIG. 6. The lower bound of the 90% CI of the GMFR in the full dose SC group is larger than 1.4 which was pre-specified to exclude a failed clinical trial. A dose-response relationship was observed in the GMFR with the intradermal route of administration. The data demonstrate that a full dose of ZOSTAVAX administered through shallow ID delivery had a 2-fold higher GMFR when compared to a full dose administered by SC delivery. The data also show that a 1/10 dose administered via shallow ID delivery yields a GMFR that is greater than a full dose administered subcutaneously.

Figure 4:
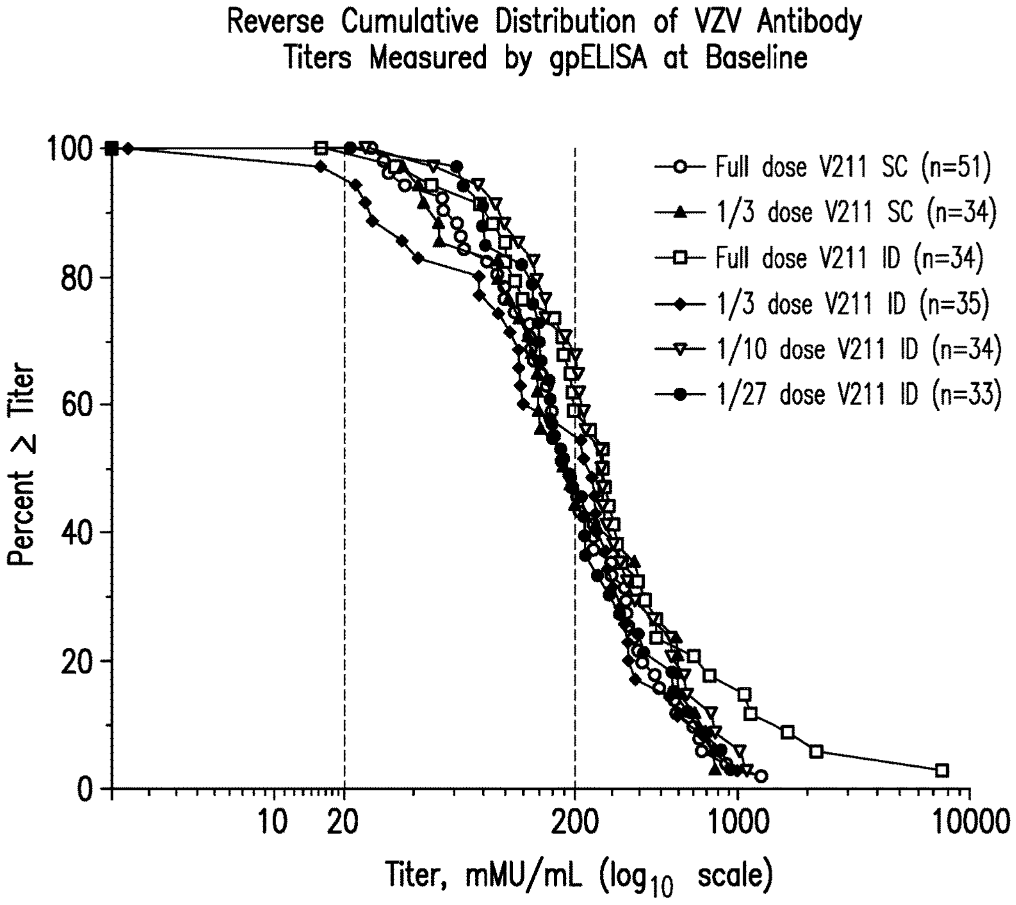
FIG. 4 shows the reverse cumulative distribution of VZV antibody titers (mMU/mL) at baseline in subjects who received a full dose or ⅓ dose of ZOSTAVAX™ subcutaneously, or a full dose, ⅓ dose, 1/10 dose or 1/27 dose of ZOSTAVAX™ through shallow intradermal delivery with the NanoPass MicronJet600™ needle hub, measured by gpELISA.
Figure 5:
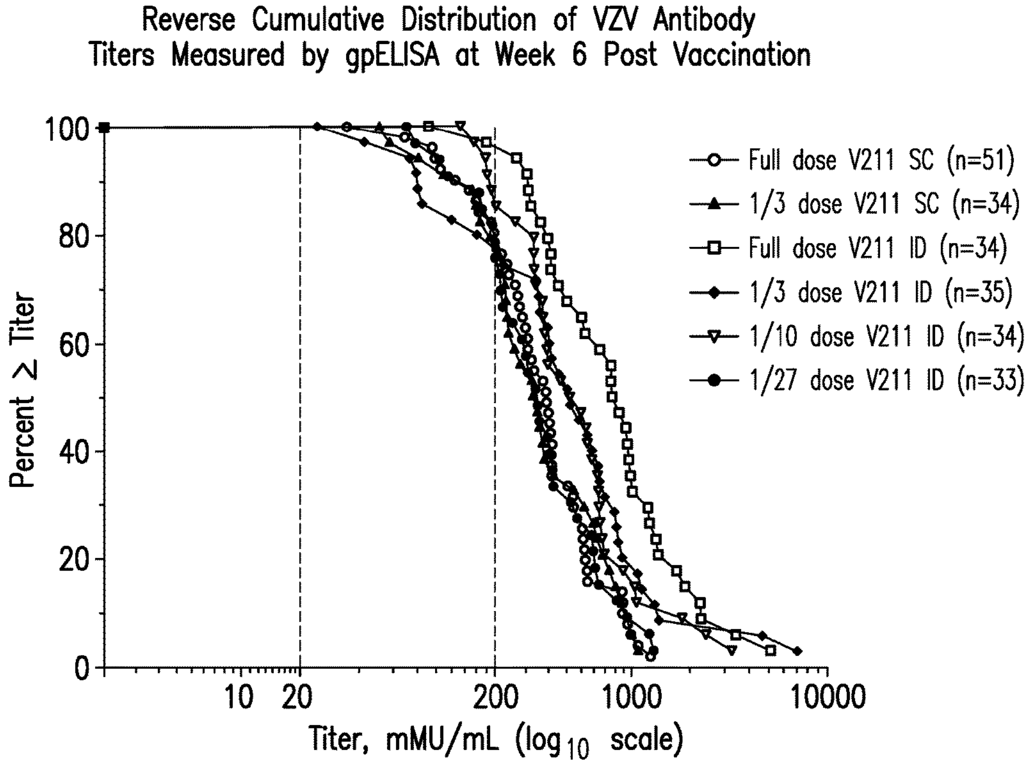
FIG. 5 shows the reverse cumulative distribution of VZV antibody titers (mMU/mL) at 6 weeks post vaccination in the same subjects shown in FIG. 4.

Subjects who received full dose of vaccine through shallow ID vaccination had the highest VZV antibody titers as measured by gpELISA at 6 weeks post-vaccination followed by subjects who received ⅓ dose shallow ID and 1/10 dose shallow ID vaccination. Subjects who received full dose SC, ⅓ dose SC, and 1/27dose shallow ID vaccination had the lowest VZV antibody titers as measured by gpELISA at 6 weeks post-vaccination. The reverse cumulative distribution of VZV antibody titers measured by gpELISA at baseline and 6 weeks post-vaccination are shown in FIGS. 4 and 5, respectively. There was no statistical imbalance in baseline mean gpELISA titers between groups. The 6 week mean titers confirm the conclusions based on GMFR (FIG. 7).

For all treatment groups other than the full dose SC group, the subjects who were ≥60 years of age had lower GMFR than those who were 50 to 59 years of age. Within each age strata, the full dose ID group had numerically higher GMFR than full dose SC and ⅓ dose SC groups, despite small sample sizes. A summary of fold-rises from baseline in VZV antibody responses measured by gpELISA at 6 weeks post-vaccination by age stratum is provided in FIG. 8.

In our previous research regarding ZOSTAVAX™, we found that low baseline gpELISA is a covariate for larger GMFR, and consequently defines a population where small differences between treatments may be more apparent. In this study, subjects who had baseline gpELISA titers less than or equal to the median value had substantially higher GMFR at 6 weeks post-vaccination than those who had baseline gpELISA titers greater than the median value (FIG. 9). In this subgroup with low baseline gpELISA titer, the full dose shallow ID group had higher nominally significant GMFR than the full dose SC group or ⅓$^{rd}$ dose SC group.

Preliminary results indicate that intradermal vaccination with ZOSTAVAX™ using the MicronJet needle results in enhanced immunogenicity relative to subcutaneous vaccination with a regular staked needle, as measured by gpELISA in adults 50 years or older. A placebo match to ZOSTAVAX™ SC was not utilized because gpELISA titers were known to be stable over this period in adults from previous work. The observed GMFR in subjects receiving full dose ZOSTAVAX™ SC was 1.74 (90% CI 1.48-2.05), lower than expected based on pivotal studies which tested immunogenicity of ZOSTAVAX™ SC.

We stratified enrollment based on age (age 50-59 vs 60 and older), based on reduced fold-rise in gpELISA titer in older subjects. Based on previous studies of ZOSTAVAX™ SC subjects age 60 and older ZOSTAVAX™ SC induced a rise of gpELISA 1.7 fold (Oxman et al., A Vaccine to Prevent Herpes Zoster and Postherpetic Neuralgia in Older Adults. *New England Journal Medicine* 352: 2271-2284 (2005)), while in this study, subjects aged 50-59 ZOSTAVAX™ SC induced a rise of 2.3 fold at 6 weeks. The slightly lower GMFR observed in this study with Full Dose SC appears to be by chance.

The two major factors that explain gpELISA titer rise include age and baseline titer. Imbalance in age was addressed with the age-stratified design. Within each age strata, the group that received a full dose of vaccine through shallow ID delivery had numerically higher GMFR than groups that received a full dose or a ⅓ dose through SC administration. Lower baseline gpELISA are associated with higher GMFR in the previous studies of ZOSTAVAX™ (Oxman et al., (2005), supra). In this study, baseline titers were similar among the dose groups. Baseline mean titer for the full dose SC group were not numerically higher than full dose shallow ID group, suggesting that baseline titer are an unlikely explanation for the slightly lower GMFR in the full dose SC group. The mean baseline gpELISA titers in this study were about 200 units/mL, lower than in previous studies of ZOSTAVAX™, with a baseline mean of about 288 units/mL.

Figure 10A:
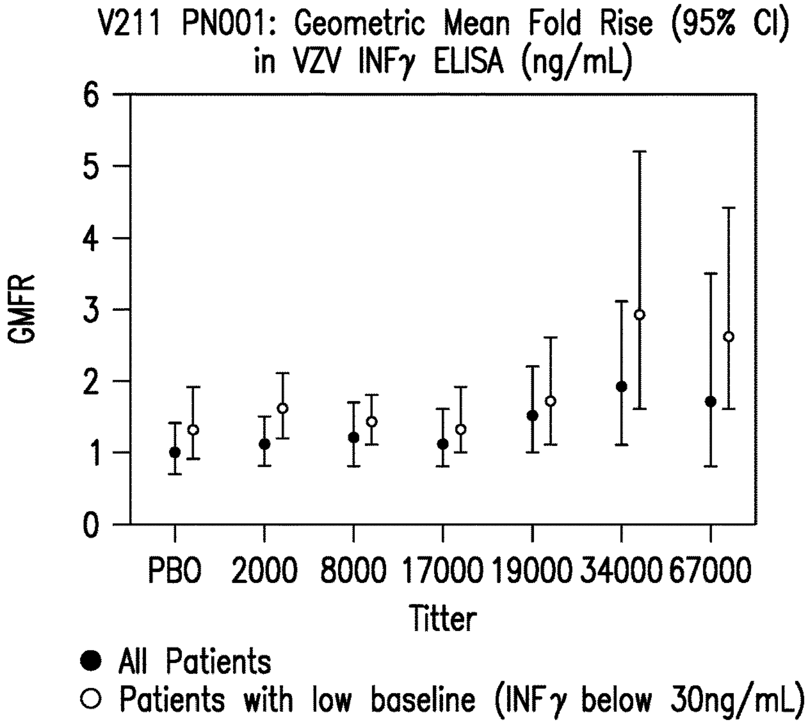
FIG. 10 shows the VZV IFNγ ELISA (panel A) and gpELISA (panel B) GMFR data. See Example 8.
Figure 10B:
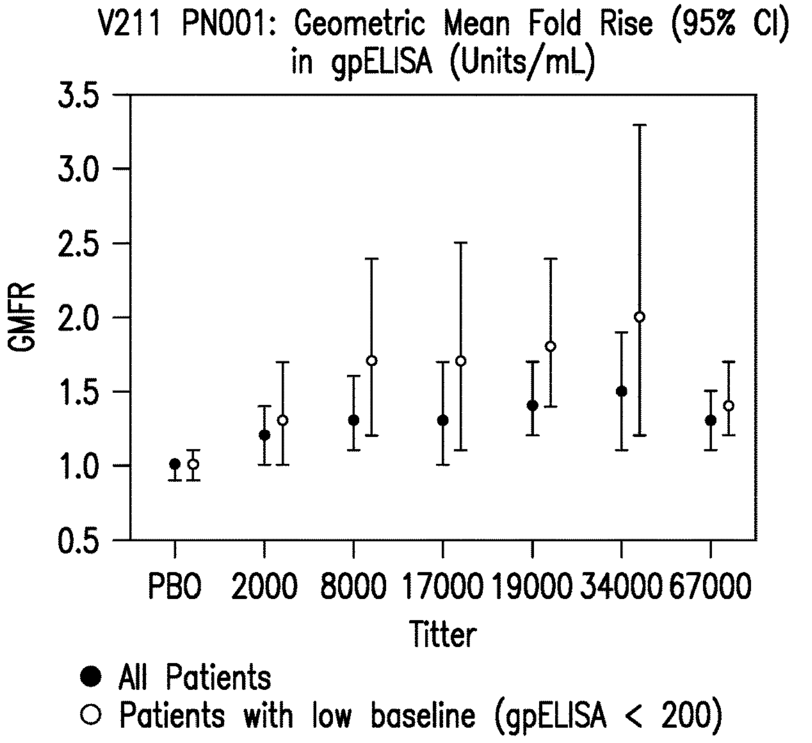

The full dose shallow ID group had nominal statistical superiority in fold-rise from baseline in gpELISA compared with the full dose SC group. A dose response was apparent for the intradermal route of administration. Chance explanations for these observations seem unlikely given age stratification and baseline titer distributions. Higher GMFR was seen for the full dose shallow ID group both within age strata, and in the subgroup defined by baseline lower gpELISA titer. Previous data with ZOSTAVAX SC do not support a dose response with SC administration across a range of virus dose from 2000 pfu to 67,000 pfu. Observations were consistent with the hypothesis that a minimum threshold of vaccine potency is required to elicit a cell mediated response (See FIG. 10).

VZV IFN-γ ELISPOT Results

The number of subjects with non-evaluable ELISPOT results at Day 1 or Day 42 was 5/223 (2%). A nonevaluable rate of 16% was anticipated based on previous studies (Oxman et al. (2005), supra). A summary of the fold-rises from baseline in VZV antibody responses measured by ELISPOT at week 6 post-vaccination are shown in FIG. 11A by treatment group. The lower bound of the 90% CI for GMFR excluded 1 for all dose groups except for the 1/27 shallow ID dose. The point estimates for ELISPOT GMFR were higher for the full dose shallow ID and ⅓ dose shallow ID groups than for the other groups. There appeared to be a dose-response relationship in the ELISPOT GMFR with the intradermal route of administration.

The point estimates of the GMFR in ELISPOT in this study ranged from 1.14 to 1.91 across the different dose groups. The 90% CI for full dose ZOSTAVAX™ administered by ID route includes the GMFR of 2.1 observed in the Shingles Prevention Study which enrolled subjects 60 years of age and greater and administered ZOSTAVAX™ or placebo by SC route (Oxman et al., (2005), supra). In that study, the ELISPOT results were stable across 6 weeks with placebo treatment, and so placebo was not included in this study.

The point estimates for ELISPOT GMFR were higher for ZOSTAVAX™ full dose ID and ⅓ dose ID groups than for other doses and routes. The baseline GMC are the lowest (by chance) for the full dose ID, ⅓ dose ID and ⅒ dose ID groups. As low baseline GMC was shown in the ZOSTAVAX™ development program to be a covariate associated with higher GMFR of ELISPOT, this fact may in part explain the numerically higher GMFR for Full dose ID and ⅓ dose ID groups. For the lowest dose tested, the 1/27 dose ID group, the 90% CI for the GMFR included 1, indicating no effect of vaccination on ELISPOT results.

Example 9

Safety of ZOSTAVAX™ Administered Intradermally or Subcutaneously

Preliminary analysis of safety data indicate that there were no serious vaccine-related adverse events (AE's), no withdrawals from the study due to AE's and no deaths. One case of VZV-like rash, which was PCR negative for HSV and VZV, was reported (see Example 4). No elevated temperatures in volunteers were observed through day 42>101° F.

In this study, we used the validated Vaccine Report Card to collect injection site reactions for the 5 days following vaccination. A larger percentage of subjects who received intradermal vaccinations reported injection site erythema and induration as compared to those who received subcutaneous vaccinations. The percentage of subjects who reported injection site pain and swelling was comparable between the 2 routes of administration. Saline placebo administered with the MicronJet™ (Nanopass Technologies, Ltd.) needle had a lower incidence of each common injection site AE than any dose of ZOSTAVAX™. Injection site reactions that occurred from Day 1 through 5 following vaccination are shown in FIG. 12.

Analysis of the Injection Experience Questionnaire ("IEQ") indicates that vaccination with the MicronJet600™ was viewed more favorably than historical injections with an ordinary hollow steel needle. 34 adult subjects received full dose ID ZOSTAVAX™ administration (and a subset of those subjects received ID placebo vaccination) by two adjacent injections in the same arm and completed the IEQ. 115 subjects who received either ⅓ dose ID ZOSTAVAX™, ⅒ dose ID ZOSTAVAX™, 1/27 dose ID ZOSTAVAX™, and/or ID placebo administration with the MicronJet600 device with a single injection and also completed the IEQ.

Subject preference was notably higher for MicronJet600™ versus the ordinary hollow steel needle (data not shown). Subjects preferred the MicronJet600™ versus the ordinary hollow steel needle for their children for future vaccinations. The majority of subjects felt that the MicronJet600™ was painless as compared to an ordinary hollow steel needle. In the full dose ID group, ~12% less subjects felt that the MicronJet600™ injection was painless versus the other lower volume doses. This increased pain observance in this group is likely related to the increased fluid volume associated with the full dose administration resulting in the need to have two separate jabs in the same arm. Finally, the majority of subjects found vaccination with the MicronJet600™ to be not intimidating or less intimidating than the ordinary hollow steel needle.

What is claimed is:

1. A method of vaccinating a patient against varicella zoster virus (VZV) infection or reactivation of latent VZV infection comprising injecting an effective amount of a live attenuated VZV vaccine to the epidermis or the dermis of the patient's skin at a depth of between 100 and 700 microns from the surface of the skin, wherein the live attenuated VZV vaccine is liquid and comprises a live attenuated VZV strain, and wherein the VZV vaccine is injected with an intradermal delivery device comprising one or more hollow needles for penetrating the skin, wherein the device is adapted for shallow intradermal delivery of the VZV vaccine.

2. The method of claim 1, wherein the method is for preventing herpes zoster (HZ) or reducing the severity or duration thereof in an individual at risk of developing HZ.

3. The method of claim 2, wherein the individual is 50 years of age or older.

4. The method of claim 2, wherein the individual is 60 years of age or older.

5. The method of claim 2, wherein from about 19,400 plaque forming units (PFUs) to about 56,000 PFUs of live VZV attenuated vaccine is administered to the patient.

6. The method of claim 1, wherein from about 9,700 PFUs to about 28,000 PFUs of live attenuated VZV vaccine is administered to the patient.

7. The method of claim 1, wherein from about 6,500 PFUs to about 18,700 PFUs of live attenuated VZV vaccine is administered to the patient.

8. The method of claim 1, wherein from about 1,940 PFUs to about 5,600 PFUs of live attenuated VZV vaccine is administered to the patient.

9. The method of claim 1, wherein the live attenuated VZV vaccine is concomitantly administered with an inactivated flu vaccine or a live attenuated flu vaccine.

10. The method of claim 1, wherein the method is for reducing the likelihood of VZV infection or preventing chicken pox or reducing the severity or duration thereof.

11. The method of claim 10, wherein the patient was not previously infected with VZV.

12. The method of claim 11, wherein the patient is between 12 months and 12 years of age.

13. The method of claim 11, wherein the patient is 13 years of age or older.

14. The method of claim 10, wherein about 1350 plaque forming units (PFU's) or greater of live attenuated VZV vaccine are administered to the patient.

15. The method of claim 11, wherein about 675 PFUs or greater of live attenuated VZV vaccine are administered to the patient.

16. The method of claim 10, wherein the patient is concomitantly administered one or more vaccines selected from the group consisting of: a measles vaccines, a mumps vaccines, a rubella vaccine, a flu vaccine, an MMR vaccine, a diphtheria vaccine, a tetanus vaccine, an acellular pertussis vaccine, a polio vaccine, and a *haemophilus* b conjugate vaccine.

17. The method of claim 1, wherein the vaccine is administered at a depth of 100 to 600 microns from the surface of the skin.

18. The method of claim 1, wherein the one or more needles are made of silicon, stainless steel, a polymer, or a biodegradable material.

19. The method of claim 1, wherein the VZV strain is the Oka strain of varicella or an Oka strain derivative.

20. The method of claim 1, wherein the method further comprises allowing a predetermined amount of time to pass, and administering to the individual a second dose of the live attenuated VZV vaccine.

21. The method of claim 20, wherein the second dose of the VZV vaccine is administered to the patient through shallow intradermal or subcutaneous delivery.

22. A method of reducing the likelihood of herpes zoster in a patient comprising injecting an effective amount of a live attenuated VZV vaccine to the epidermis or the dermis of the patient's skin at a depth of between 100 and 700 microns from the surface of the skin wherein the live attenuated VZV vaccine is liquid and comprises a live attenuated VZV strain, and wherein the VZV vaccine is injected with an intradermal delivery device comprising one or more hollow needles for penetrating the skin, wherein the device is adapted for shallow intradermal delivery of the VZV vaccine.

23. A method of inducing an immune response against varicella zoster virus in a patient comprising injecting an effective amount of a live attenuated VZV vaccine to the epidermis or the dermis of the patient's skin at a depth of between 100 and 700 microns from the surface of the skin, wherein the live attenuated VZV vaccine is liquid and comprises a live attenuated VZV strain, and wherein the VZV vaccine is injected with an intradermal delivery device comprising one or more hollow needles for penetrating the skin, wherein the device is adapted for shallow intradermal delivery of the VZV vaccine.

* * * * *